United States Patent
Deitch et al.

(10) Patent No.: US 8,398,659 B2
(45) Date of Patent: Mar. 19, 2013

(54) METHOD OF INTRACORPOREALLY SUTURING TISSUE

(75) Inventors: Sarah J. Deitch, Minneapolis, MN (US);
Daniel J. Dravis, Eau Claire, WI (US);
Christopher A. Thierfelder, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 329 days.

(21) Appl. No.: 12/723,854

(22) Filed: Mar. 15, 2010

(65) Prior Publication Data
US 2011/0224697 A1   Sep. 15, 2011

(51) Int. Cl.
*A61B 17/04* (2006.01)
*A61B 17/12* (2006.01)

(52) U.S. Cl. ........................................ 606/144
(58) Field of Classification Search .................. 606/144
See application file for complete search history.

(56) References Cited

U.S. PATENT DOCUMENTS

| | | | |
|---|---|---|---|
| 4,345,601 A | 8/1982 | Fukuda | |
| 5,333,624 A | 8/1994 | Tovey | |
| 5,376,101 A | 12/1994 | Green et al. | |
| 5,665,109 A | 9/1997 | Yoon | |
| 5,990,378 A * | 11/1999 | Ellis | 623/11.11 |
| 6,551,330 B1 | 4/2003 | Bain et al. | |
| 6,582,443 B2 | 6/2003 | Cabak et al. | |
| 6,612,977 B2 | 9/2003 | Staskin et al. | |
| 6,872,227 B2 | 3/2005 | Sump et al. | |
| 7,544,199 B2 * | 6/2009 | Bain et al. | 606/144 |
| 8,043,205 B2 * | 10/2011 | MacLean | 600/37 |
| 2002/0082619 A1 | 6/2002 | Cabak et al. | |
| 2003/0004580 A1 | 1/2003 | Sump et al. | |
| 2006/0015069 A1 | 1/2006 | Evans et al. | |
| 2006/0229493 A1 | 10/2006 | Weiser et al. | |
| 2006/0229596 A1 | 10/2006 | Weiser et al. | |
| 2006/0252980 A1 | 11/2006 | Arnal et al. | |
| 2007/0015953 A1 | 1/2007 | MacLean | |
| 2007/0021649 A1 | 1/2007 | Nowlin et al. | |
| 2007/0055095 A1 | 3/2007 | Chu et al. | |
| 2009/0099409 A1 | 4/2009 | Luehrs et al. | |
| 2009/0105743 A1 | 4/2009 | Chu | |
| 2009/0216072 A1 | 8/2009 | Zipper | |

(Continued)

FOREIGN PATENT DOCUMENTS

| | | |
|---|---|---|
| WO | 99/59477 A1 | 11/1999 |
| WO | 2006/108145 A1 | 10/2006 |
| WO | 2006108144 A2 | 10/2006 |
| WO | 2007002012 A1 | 1/2007 |

(Continued)

OTHER PUBLICATIONS

Capio Brochure from Boston Scientific, Transvaginal Suture Capturing Device, 2000.

*Primary Examiner* — Melanie Tyson
(74) *Attorney, Agent, or Firm* — Coloplast Corp., Coloplast A/S; Daniel G. Chapik; Nicholas R. Baumann

(57) ABSTRACT

A method of intracorporeally suturing a patient includes engaging tissue with a suturing head retaining a needle, forming an opening in the tissue with the needle, and pushing the needle into a through-bore formed in a capsule that is attached to a leading end of a suture and pulling the capsule and the leading end of a suture through the opening. The method additionally includes securing a clasp attached to a trailing end of the suture to an implantable support, and pulling on the suture and implanting the support inside the patient.

14 Claims, 20 Drawing Sheets

U.S. PATENT DOCUMENTS

| | | |
|---|---|---|
| 2009/0216075 A1 | 8/2009 | Bell et al. |
| 2009/0216253 A1* | 8/2009 | Bell et al. ............ 606/153 |
| 2009/0221867 A1* | 9/2009 | Ogdahl et al. ............ 600/37 |
| 2009/0222027 A1 | 9/2009 | Sauer |
| 2009/0228021 A1 | 9/2009 | Leung |
| 2009/0264698 A1 | 10/2009 | Arnal et al. |

FOREIGN PATENT DOCUMENTS

| | | |
|---|---|---|
| WO | 2007/109508 A1 | 9/2007 |
| WO | 20070146784 A2 | 12/2007 |
| WO | 2008/057261 A2 | 5/2008 |
| WO | 2008/067317 A2 | 6/2008 |
| WO | 2008085825 A1 | 7/2008 |

* cited by examiner

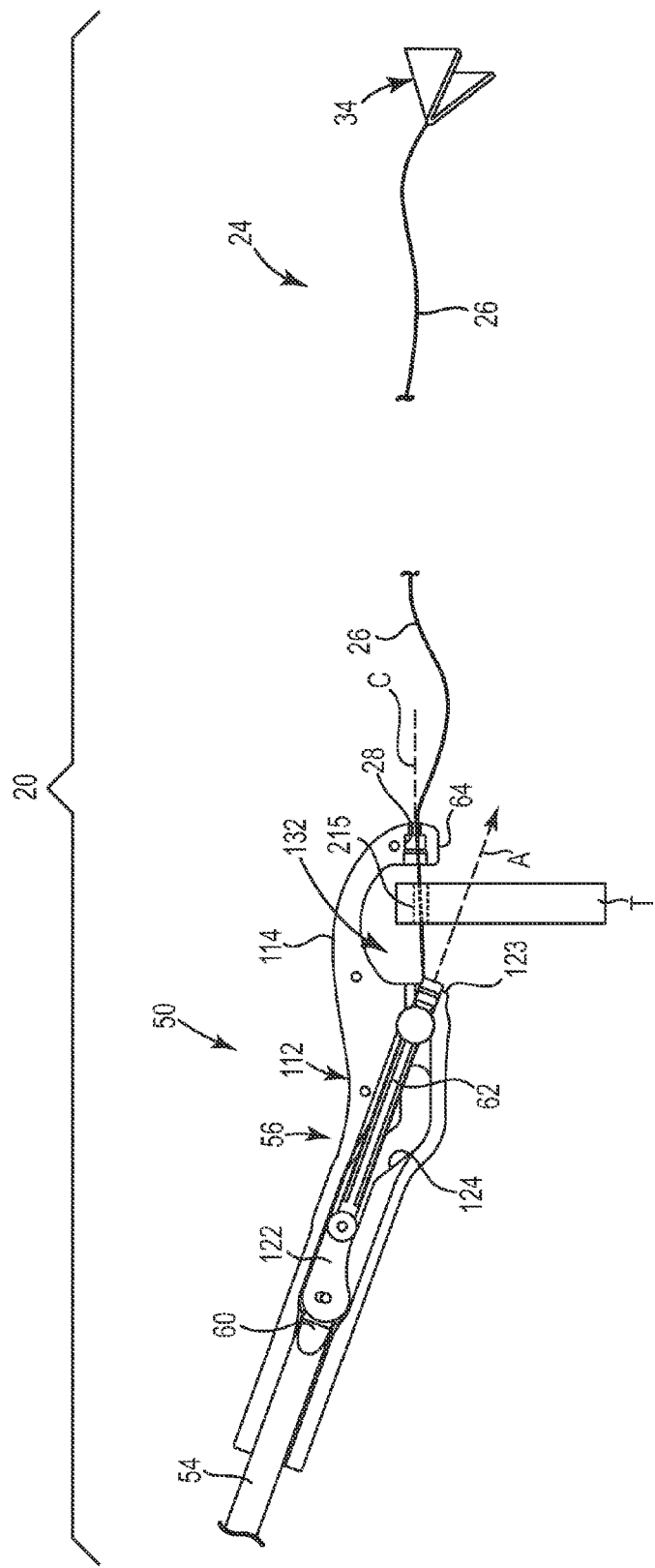

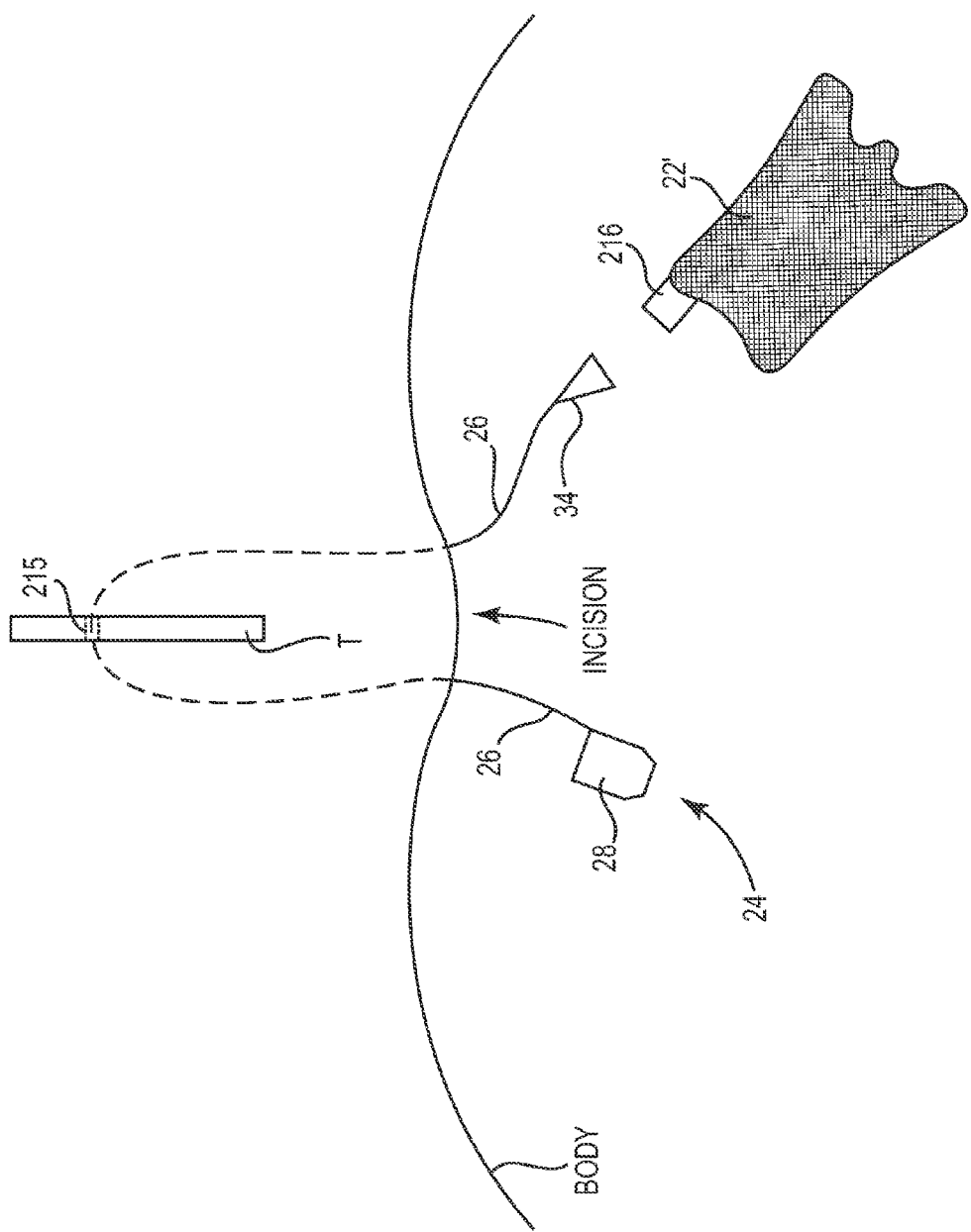

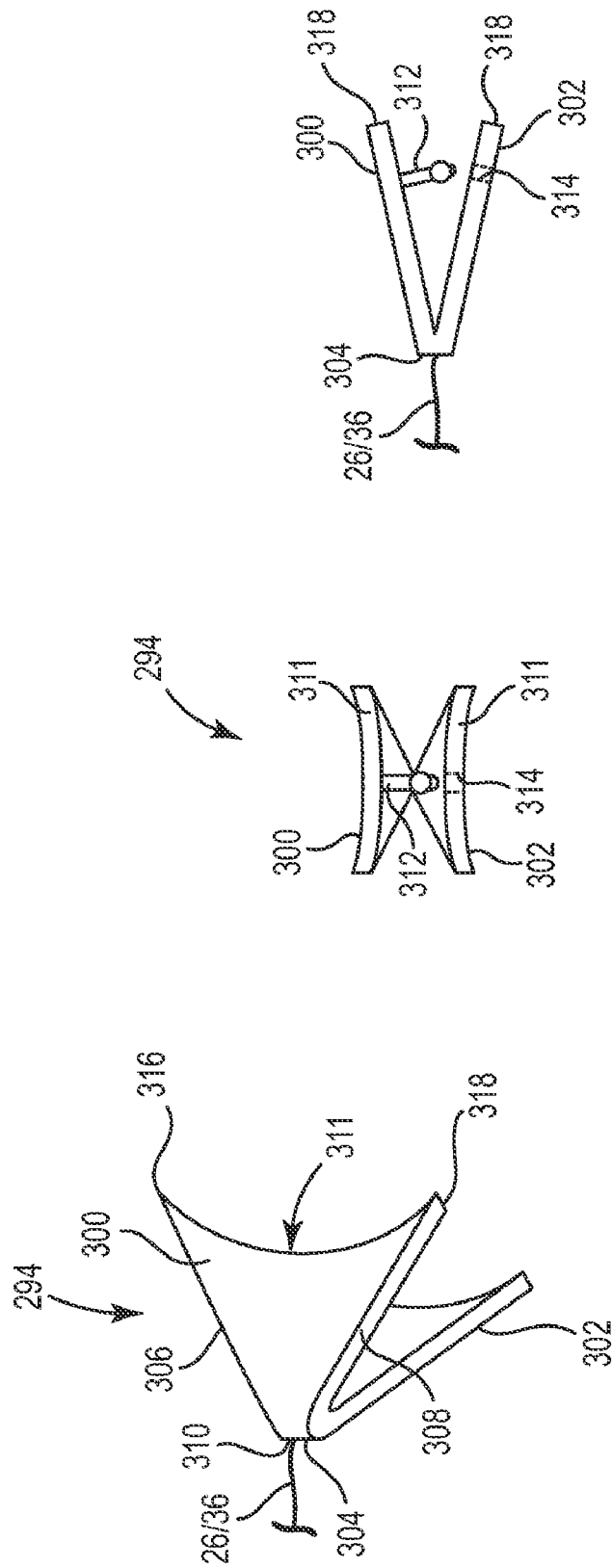

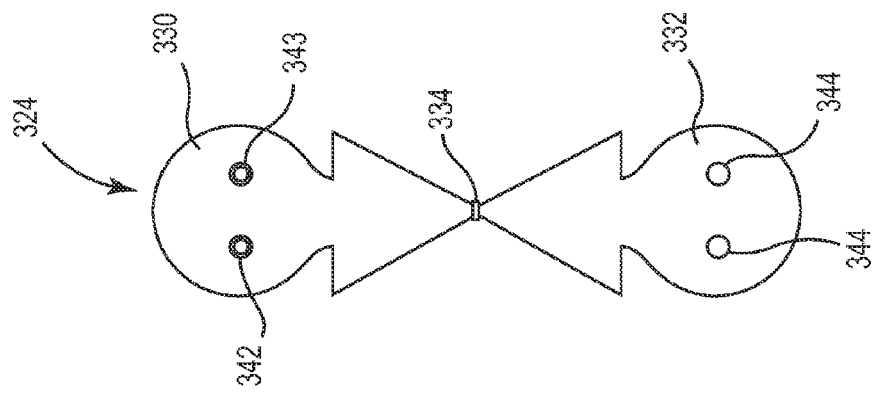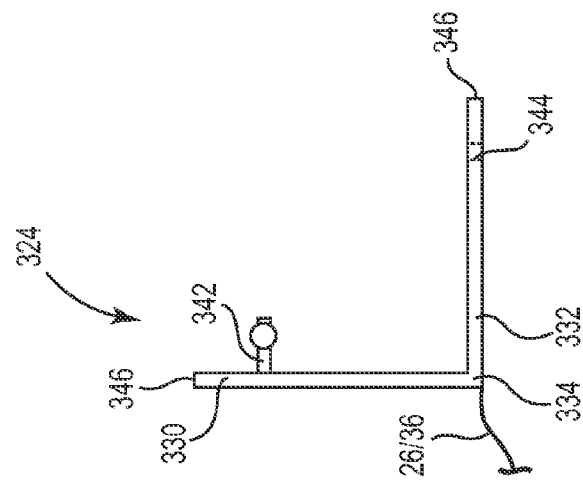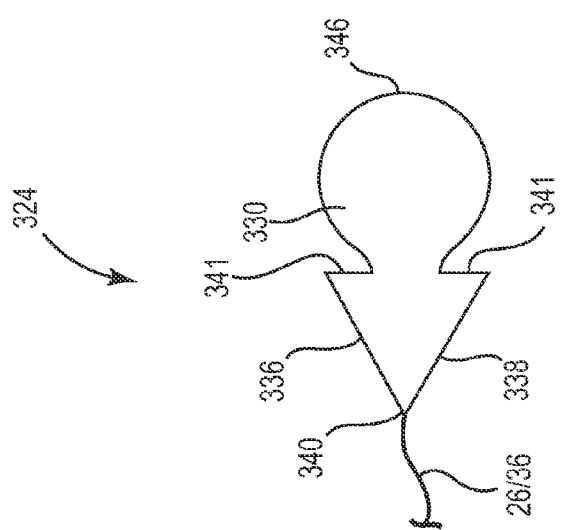
Fig. 11C
Fig. 11B
Fig. 11A

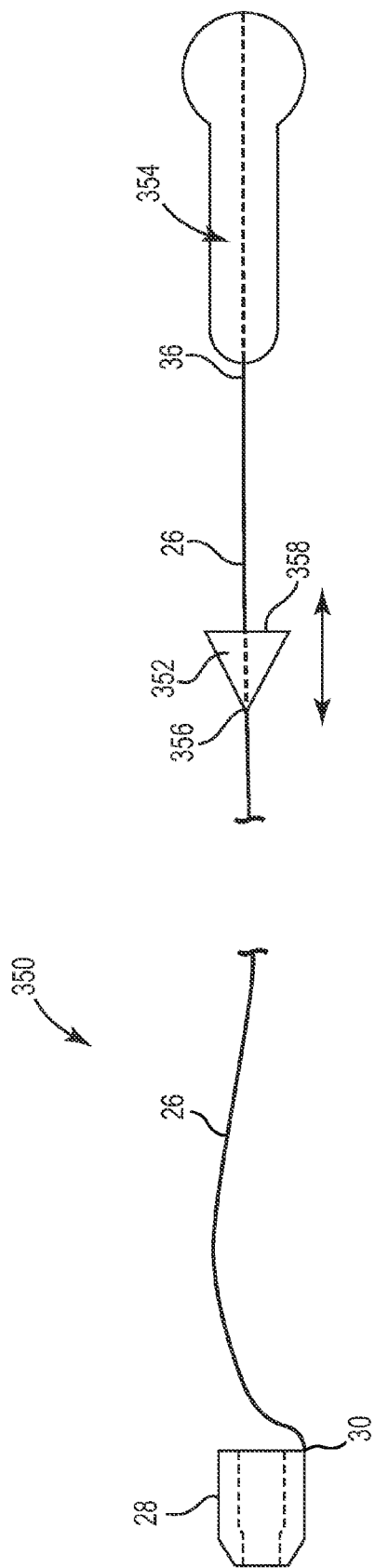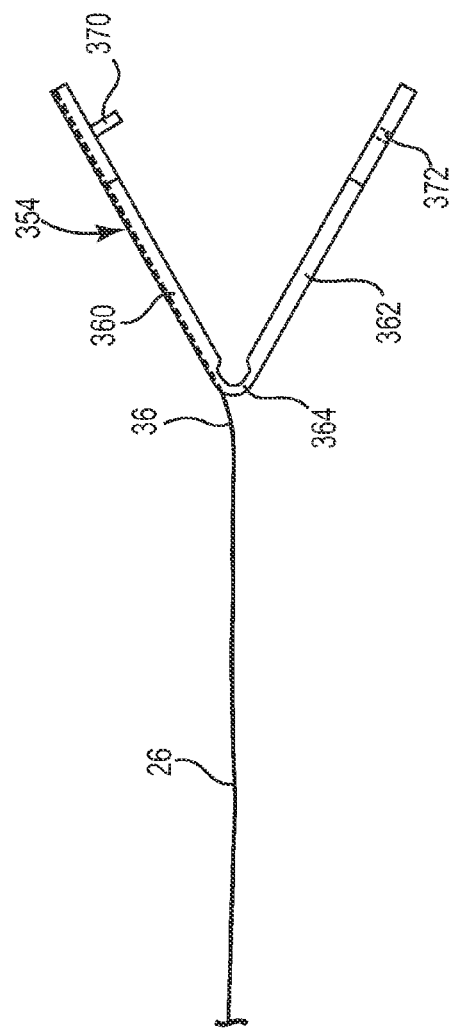
Fig. 12A
Fig. 12B

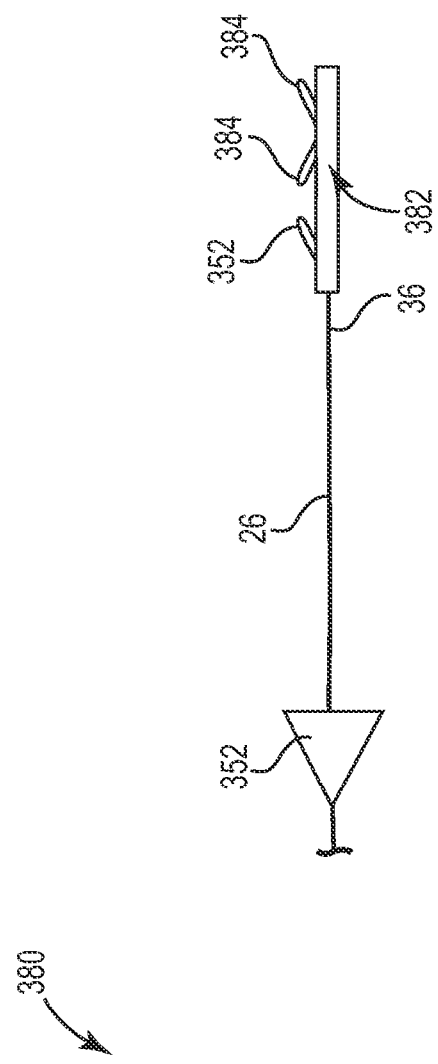
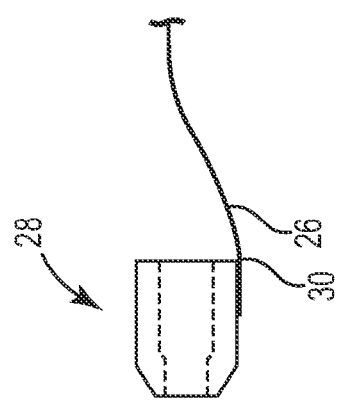
Fig. 13

METHOD OF INTRACORPOREALLY SUTURING TISSUE

BACKGROUND

Intracorporeal suturing of tissue during surgery presents challenges to the surgeon in that the surgeon is called upon to manipulate suturing instruments within the confines of a relatively small incision formed in the patient's body.

For example, in some cases a surgeon will place a suture within the pelvis of the patient without actually seeing the suture site. The challenge of placing a suture within the pelvic region is compounded when additional support structures are sutured into the pelvic region, for example when the pelvis is reinforced with a mesh-style support to address pelvic organ prolapse or urinary incontinence.

Improved suturing instruments and improved methods of delivering intracorporeal sutures would be welcomed by the surgical staff.

SUMMARY

One aspect provides an attachment assembly configured to secure an implantable support within a patient. The attachment assembly includes a length of suture, an anchor, a capsule, and a clasp. The suture has a leading end half terminating in a leading end and a trailing end half terminating in a trailing end. The anchor is coupled to the trailing end half of the length of the suture. The capsule is attached to the leading end of the suture and has a through-bore extending longitudinally through the capsule. The clasp is attached to the trailing end of the suture, the clasp attachable to the implantable support.

One aspect provides a method of intracorporeally suturing a patient includes engaging tissue with a suturing head retaining a needle, forming an opening in the tissue with the needle, and pushing the needle into a through-bore formed in a capsule that is attached to a leading end of a suture and pulling the capsule and the leading end of a suture through the opening. The method additionally includes securing a clasp attached to a trailing end of the suture to an implantable support, and pulling on the suture and implanting the support inside the patient.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8C is a schematic view of the needle engaged with a through-bore of the capsule and pulling the capsule and the suture through the opening formed in the intracorporeal tissue.

FIGS. 8F-8I are schematic views of embodiments of the suture attachment assembly employed to place another implantable fabric into intracorporeal tissue.

FIG. 10A is a perspective view, FIG. 10B is a front view, and FIG. 10C is a side view of one embodiment of a clasp suited for use with the suture attachment assembly illustrated in FIG. 1.

FIG. 11A is a top view, FIG. 11B is a side view, and FIG. 11C is a perspective view of one embodiment of a clasp suited for use with the suture attachment assembly illustrated in FIG. 1.

FIG. 12A is a top view and FIG. 12B is a side view of another embodiment of a suture attachment assembly.

FIG. 13 is a side view of another embodiment of a suture attachment assembly.

DETAILED DESCRIPTION

Figure 1:
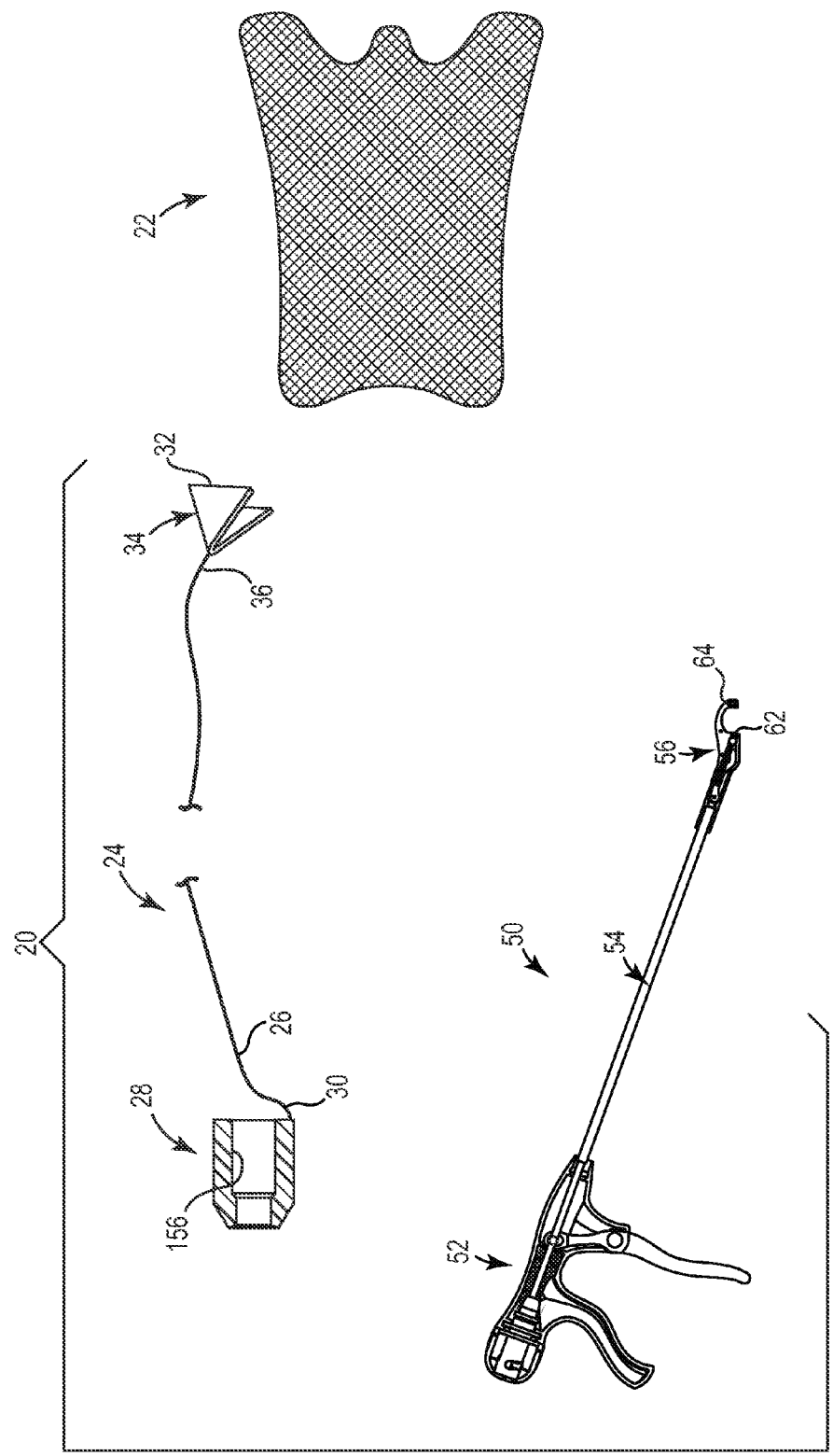
FIG. 1 is a schematic view of one embodiment of an implantable support attachment system including a suture thrower and a suture attachment assembly.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

It is desirable to implant support materials to address pelvic dysfunction. Some systems that are employed to implant support materials include a needle attached to a mesh support by a suture line. The suture line can include a tapered portion having one segment that is wider than a second statement, or the wider segment is employed as a dilator to force the tissue open wide enough to accept a portion of the mesh support. The dilation of the tissue has the potential to undesirably weaken or traumatize the tissue.

In contrast, embodiments of a suture attachment system and assembly are described herein that obviate the dilation of the tissue and offer improved implant management that is less complex, or intuitive, and less cumbersome.

Embodiments provide a suture attachment assembly that is configured to cooperate with a suture thrower to allow a surgeon to secure an implantable support within a patient. The suture attachment assembly includes a suture having a clasp opposite a leading end. The clasp is configured to quickly engage with the support, obviating the use of knots. The clasp allows the surgeon to conveniently place (and if desired, replace) the clasp onto the support at a location outside of the patient's body. The leading end is configured to be directed through an opening in intracorporeal tissue to pull the clasp/support along in the wake of the suture. In one embodiment, an anchor of the attachment assembly is terminated against the intracorporeal tissue to secure the implantable support at a desired location inside the patient.

In one embodiment, a suture thrower is provided that has a movable needle that moves in a proximal direction to first form an opening in the tissue and subsequently capture the capsule, which is retracted by the needle in the distal direction to allow the surgeon to retrieve the capsule and the suture attached to the capsule to a location outside of the patient's body.

FIG. 1 is a schematic view of one embodiment of an attachment system 20 configured to secure an implantable support 22 within a patient. The attachment system 20 includes a suture attachment assembly 24 and a suture thrower 50. As noted above, the components of the system 20 are not drawn to scale.

The suture attachment assembly 24 has a clasp 34 that is attachable to the implantable support 22, for example outside of the patient's body by means of a quick connect or other attachment device. The suture 26 is passed through tissue and retrieved to place the support 22 intracorporeally at a desired location within the patient. The suture attachment assembly 24 includes an anchor 32 that secures the support 22 at the desired location after the suture is retrieved through the tissue. The suture thrower 50 cooperates with the suture attachment assembly 24 to form an opening in the tissue and retrieve the suture 26 through the opening formed in the tissue.

The implantable support 22 is sized and configured to reinforce the floor of the pelvis or support other tissues within the pelvis and suitably includes nonwoven materials such as autograft material (the patient's own tissue), allograft material (tissue from a cadaver), xenograft material (tissue from another species), or synthetic materials such as woven fabrics or meshes, nonwoven fabrics or meshes, fibrillated fibers, or spun and/or fibrillated fibers. The support 22 is generally provided with voids (pores) that are configured to allow tissue ingrowth into and through the support 22. The pores of the support 22 are generally larger than, on average, about 75 µm.

In one embodiment, the implantable support 22 is a knitted monofilament polypropylene mesh having an area of approximately 225 $cm^2$ mesh with a basis weight of approximately 21 $g/m^2$, a pore size of approximately 1121 µm, and a thickness of approximately 260 µm. The mesh is thin and light weight (i.e., the basis weight is less than approximately 30 $g/m^2$) to provide a thin and comfortable mesh that is less likely to erode tissue that contacts the mesh and less likely to be sensed through the tissue layers by the patient. Other suitable materials for implantable support 22 include fabrics formed from polyester, polyethylene, silicone, urethanes, polyurethanes, copolymers, or block copolymers of these or suitably similar polymeric materials. Suitable polypropylene mesh is available from Coloplast Corp., Minneapolis, Minn. Other suitable support material is available from, for example, HerniaMesh, Chivasso, Italy.

The suture attachment assembly 24 includes a length of suture 26, a capsule 28 attached to a leading end 30 of the suture 26, an anchor 32 coupled to the suture 26, and the clasp 34 attached to a trailing end 36 of the suture 26.

In one embodiment, the suture 26 has a leading end half terminating in the leading end 30 and a trailing end half terminating in the trailing end 36, where the anchor 32 is coupled to the trailing end half of the suture 26, the capsule 28 is attached to the leading end 30 of the suture 26, and the clasp 34 is attached to the trailing end 36 of the suture 26.

In one embodiment, the capsule 28 is a tube having a through-bore 156 formed longitudinally through the capsule 28.

The suture thrower 50 includes a shaft 54 coupled between a handle 52 and a suturing head 56 that houses a movable needle 62. The handle 52 thus defines a proximal end of the suture thrower 50 and is nearest a user of the suture thrower 50. The capsule 28 is sized for retention within a distal end 64 of the suturing head 56 and the clasp 34 trails behind the suture 26 and is attachable to the implantable support 22.

During use, the handle 52 is activated to drive the needle 62 in a proximal direction to form an opening in intracorporeal tissue (for example a ligament) and subsequently seat the needle 62 into the through-bore 156 to engage the capsule 28. The needle 62 retrieves the capsule 28 through the opening in the tissue to deliver the leading end 30 of the suture 26 outside of the patient. The clasp 34, attached to the trailing end 36 of the suture 26, is available outside of the patient and accessible by the surgeon for attachment of the clasp 34 to the implantable support 22. The clasp 34, by being accessible outside of the patient's body, permits the surgeon to more accurately attach the suture 26/clasp 34 to the implantable support 22 prior to implanting the support 22 within the patient. The surgeon pulls on the capsule 28 end of the suture 26 to pull the suture 26 through the tissue and draw the implantable support 22 into the patient. The clasp 34 moves through the opening in the tissue formed by the needle 62 until the anchor 32 engages with the tissue to prevent the implantable support 22 from being withdrawn back through the opening, thus intracorporeally placing the support 22 in the patient. The surgeon subsequently removes the capsule 28 and any excess length of the suture 26 from the patient.

Figure 2:
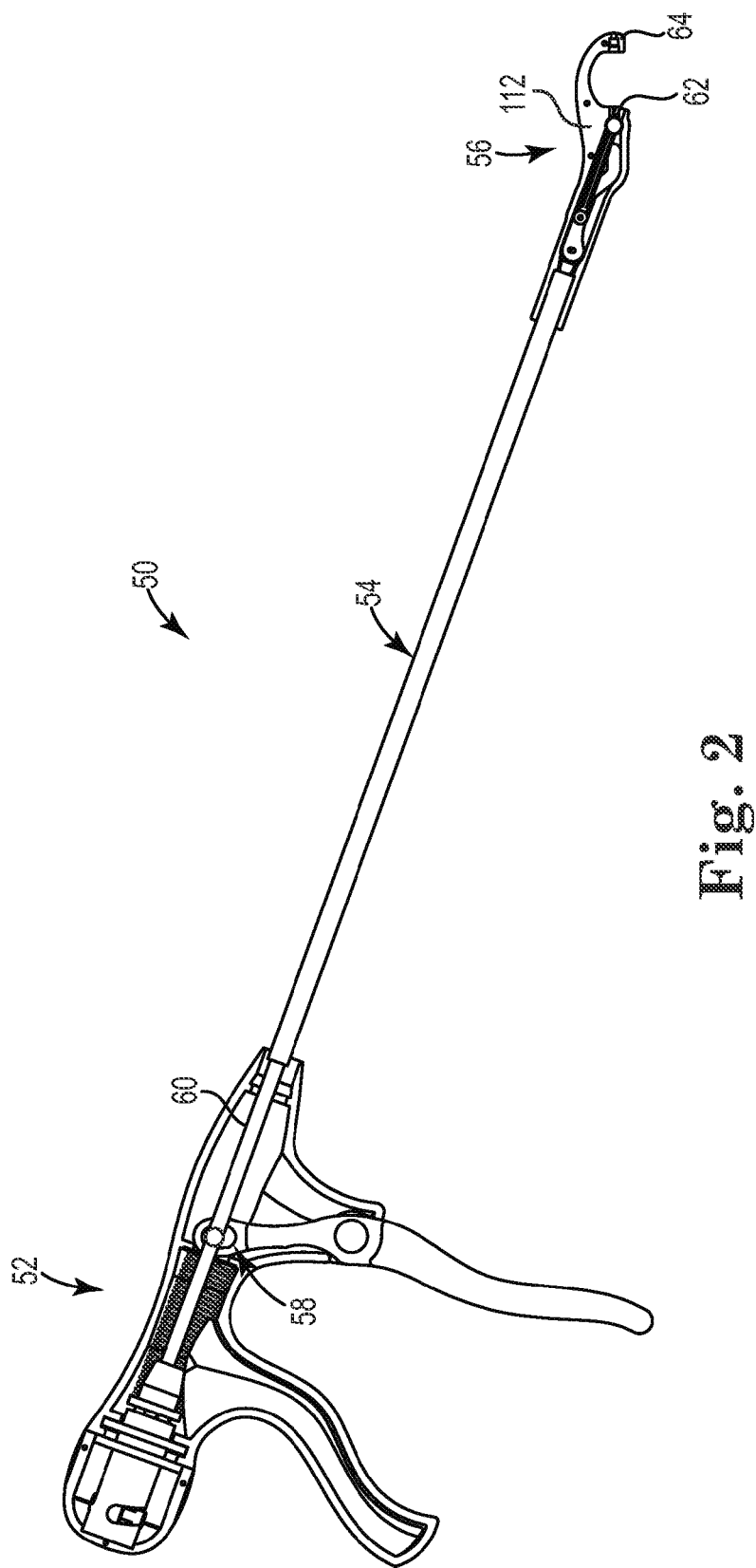
FIG. 2 is a schematic side view of one embodiment of the suture thrower illustrated in FIG. 1.

FIG. 2 is a schematic side view of the suture thrower 50. In one embodiment, handle 52 includes an actuator 58 communicating with a rod 60 that is disposed within shaft 54. When actuator 58 is activated, rod 60 moves through shaft 54 to extend the needle 62 that is stored within a proximal end portion 112 of head 56 axially outward through tissue and toward a distal end 64 of head 56. The needle 62 moves away from the user (who is holding handle 52 at the proximal end of suture thrower 50) toward distal end 64 of suture thrower 50 for engagement with the through-bore 156 formed in the capsule 28 (FIG. 1).

In one embodiment, the capsule 28 (FIG. 1) is retained within distal end 64 of the head 56 and so positioned to allow the needle 62 to frictionally engage with the through-bore 156. The needle 62 thus mates with the capsule 28, removes the capsule 28 from distal end 64, and retracts the capsule into the proximal end portion 112 of head 56. In this manner, the suture 26 that is towed behind the capsule 28 is "thrown" through the tissue. Embodiments described below include a guide pin located within head 56 that is configured to disengage the capsule 28 from needle 62 after the capsule 28 is delivered to a location outside of the patient's body.

Suture thrower 50 is suited for the intracorporeal suturing of tissue during surgery, and in one embodiment is provided as a sterile disposable surgical instrument that is discarded after the surgical procedure. To this end, the components of suture thrower 50 are selected to be compatible with gas, steam, or radiation sterilization.

Figure 3:
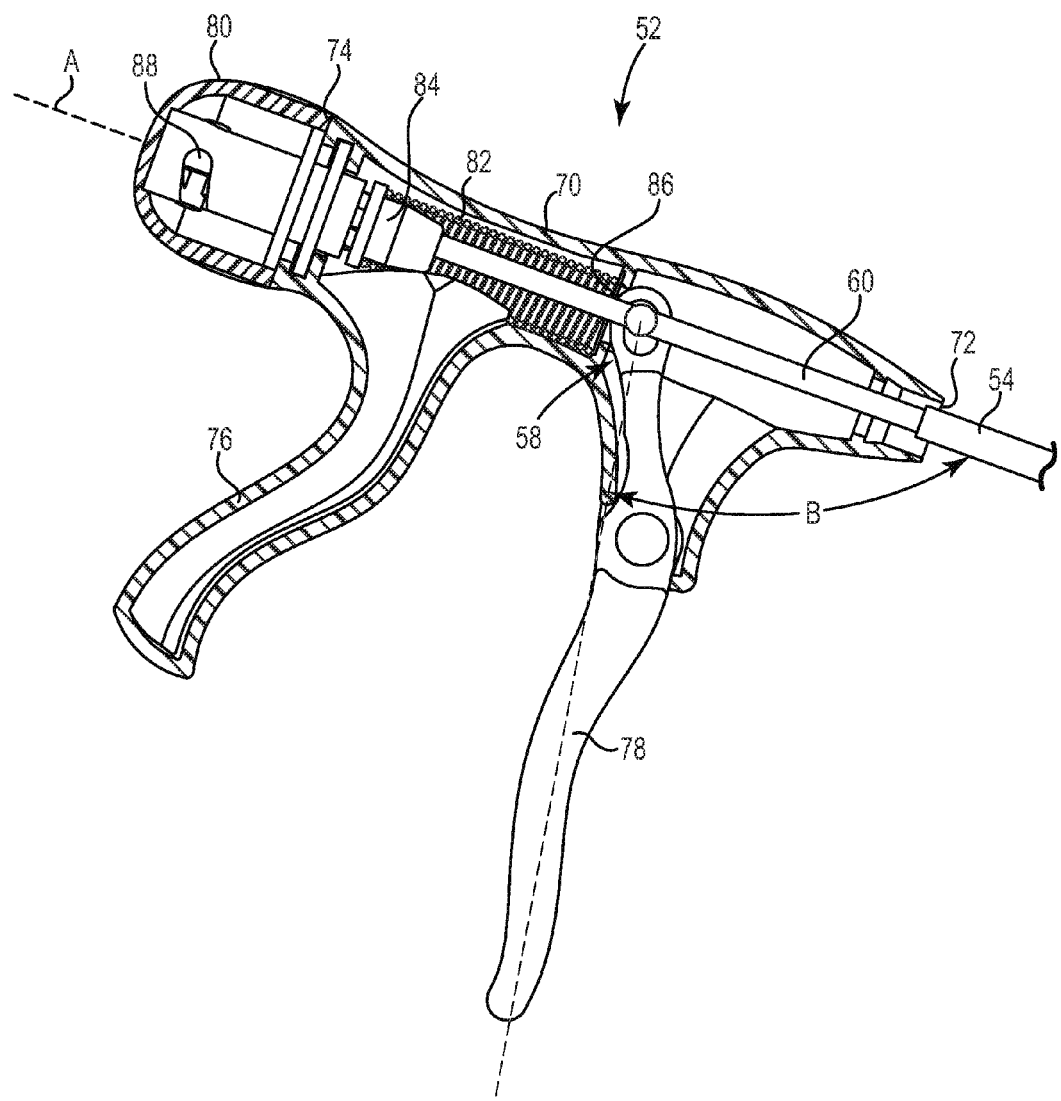
FIG. 3 is a cross-sectional view of a handle of the suture thrower illustrated in FIG. 2.

FIG. 3 is a cross-sectional view of the handle 52. In one embodiment, handle 52 is aligned with a major longitudinal axis A and includes a body 70 extending between a distal end 72 and a proximal end 74, a thumb brace 76 extending laterally from body 70, a trigger 78 spaced apart from thumb brace 76, and a knob 80 coupled to proximal end 74.

In one embodiment, body 70 is fabricated from plastic, for example via molding. Suitable plastic materials for the fabrication of body 70, brace 76, and knob 80 include, as examples, polycarbonate, polyethylene, acrylonitrile butadiene styrene, acrylic, or nylon. In one embodiment, brace 76 is integrally molded with a clamshell-style of body 70 and these two components are joined together to retain trigger 78 and knob 80. Trigger 78 is formed to have sufficient strength to resist bending when activated by the human hand. Suitable materials for forming trigger 78 include metal such as aluminum or plastics such as polyetherimide or poly-ether-etherketone.

Shaft 54 is coupled to distal end 72 of body 70, and rod 60 is disposed within shaft 54 and coupled to trigger 78. In one embodiment, actuator 58 includes trigger 78 attached to rod 60 and a spring 82 disposed within a spring pusher 84 and biased against and an internal rib 86. Trigger 78 is movable toward thumb brace 76 to move rod 60 in a distal direction longitudinally within shaft 54, which compresses spring 82. When trigger 78 is released, spring 82 extends to push spring pusher 84 proximally, which retracts or returns rod 60 toward proximal end 74. Trigger is spaced apart from thumb brace 76 by a distance of approximately 4-12 cm to enable the fingers of the user to comfortably activate trigger 78. Trigger 78 is disposed at an angle B relative to the longitudinal axis A of body 70, and in an exemplary embodiment the angle B is between 70-110 degrees such that trigger 78 is approximately orthogonal to longitudinal axis A.

Actuator 58 is configured to move rod 60 forward in a distal direction and rearward in a proximal direction within shaft 54. In one embodiment, it is desirable to move rod 60 rearward an additional distance to disengage the capsule 28 (FIG. 1) from needle 62 (FIG. 2). To facilitate this, rod 60 includes an insert (not shown) that communicates through spring pusher 84 and is captured in window 88. When knob 80 is turned, spring pusher 84 turns and the insert attached to rod 60 is retracted back in a proximal direction due to the angle of window 88, which retracts rod 60 an additional distance into body 70. For example, in one embodiment knob 80 is configured such that a 180 degree clockwise of knob 80 relative to end 74 draws rod 60 an additional distance of about 2 mm into body 70. Although knob 80 is configured to retract rod 60 further into body 70 via a turning motion, other mechanisms such as levers or draw bars for retracting rod 60 incrementally rearward are also acceptable.

Figure 4:
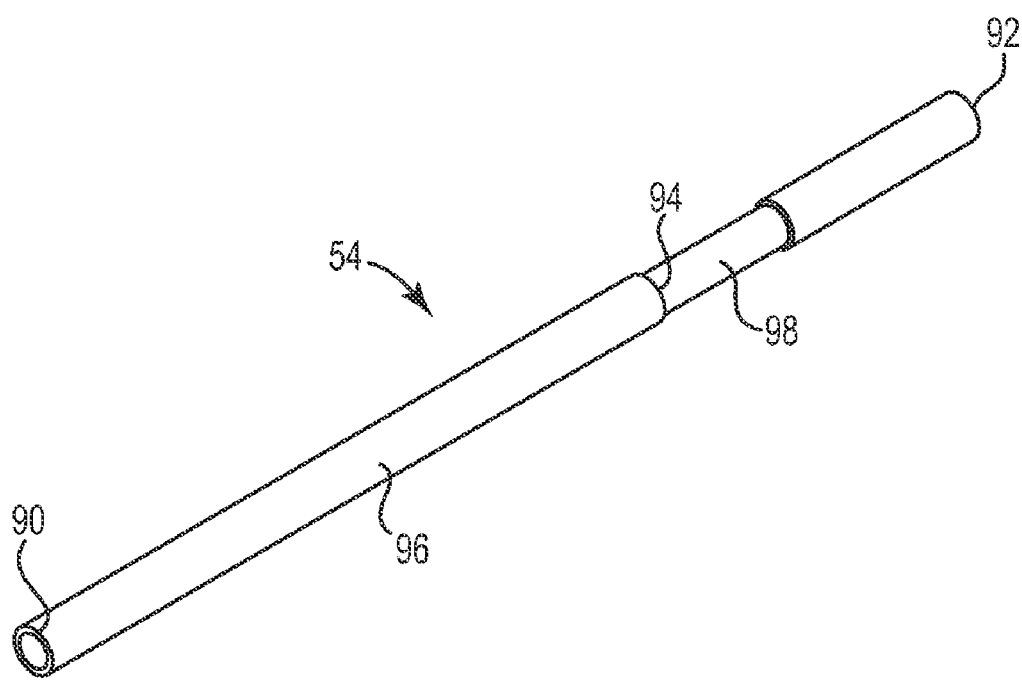
FIG. 4 is a perspective view of a shaft of the suture thrower illustrated in FIG. 2.

FIG. 4 is a side view of shaft 54. One suitable embodiment of shaft 54 includes a substantially rigid aluminum annular tube extending between a proximal end 90 that is attachable to handle 52 (FIG. 3) and a distal end 92 that is attachable to head 56. Other substantially rigid materials, such as stainless steel, are also suitable selections for fabricating shaft 54. Another embodiment of shaft 54 includes a distal end portion associated with distal end 92 that is flexible and configured to bend laterally relative to first section 96 to enable the surgeon to selectively direct head 56 to a desired location.

In one embodiment, the shaft 54 includes the proximal end 90 that is attachable to handle 52 (FIG. 3), the distal end 92 that is attachable to head 56 (FIG. 2), and a crimp 94 or a weld 94 that connects a first section 96 to a second section 98. In one embodiment, shaft 54 is formed as a thin-walled tube with first section 96 formed of a first material and a second section 98 is formed of a different second material. In an exemplary embodiment, first section 96 is formed of 6000 series aluminum and a second section 98 is formed of 3000 series aluminum, with these two metal sections 96, 98 joined together by crimp/weld 94. The 6000 series aluminum is selected to have a shear modulus of a sufficient value to preclude the user from bending first section 96 as suture thrower 50 is manipulated. For example, in one embodiment the shear modulus of first section 96 is approximately 30 $GN/m^2$. The 3000 series aluminum is selected to have a shear modulus of a sufficient value to enable a user to bend the second section 98 with their hands, which enables the user to shape and guide second section 98 (which is attached to head 56) in controlling and guiding the placement of sutures with head 56. For example, in one embodiment the shear modulus of second section 98 is approximately 10 $GN/m^2$. In another example, in one embodiment the yield strength of first section 96 is approximately 30 $GN/m^2$. The 3000 series aluminum is selected to have a yield strength of a sufficient value to enable a user to bend the second section 98 with their hands, which enables the user to shape and guide second section 98 (which is attached to head 56) in controlling and guiding the placement of sutures with head 56. For example, in one embodiment the yield strength of second section 98 is approximately 10 $GN/m^2$.

One example of suitable lengths for sections 96, 98 is for first section 96 to have a length between 4-24 cm and second section 98 to have a length from 1-10 cm. Other lengths for sections 96, 98 are also acceptable. In one embodiment, crimp/weld 94 is provided as a metal peripheral crimp securing first section 96 to second section 98.

Figure 5:
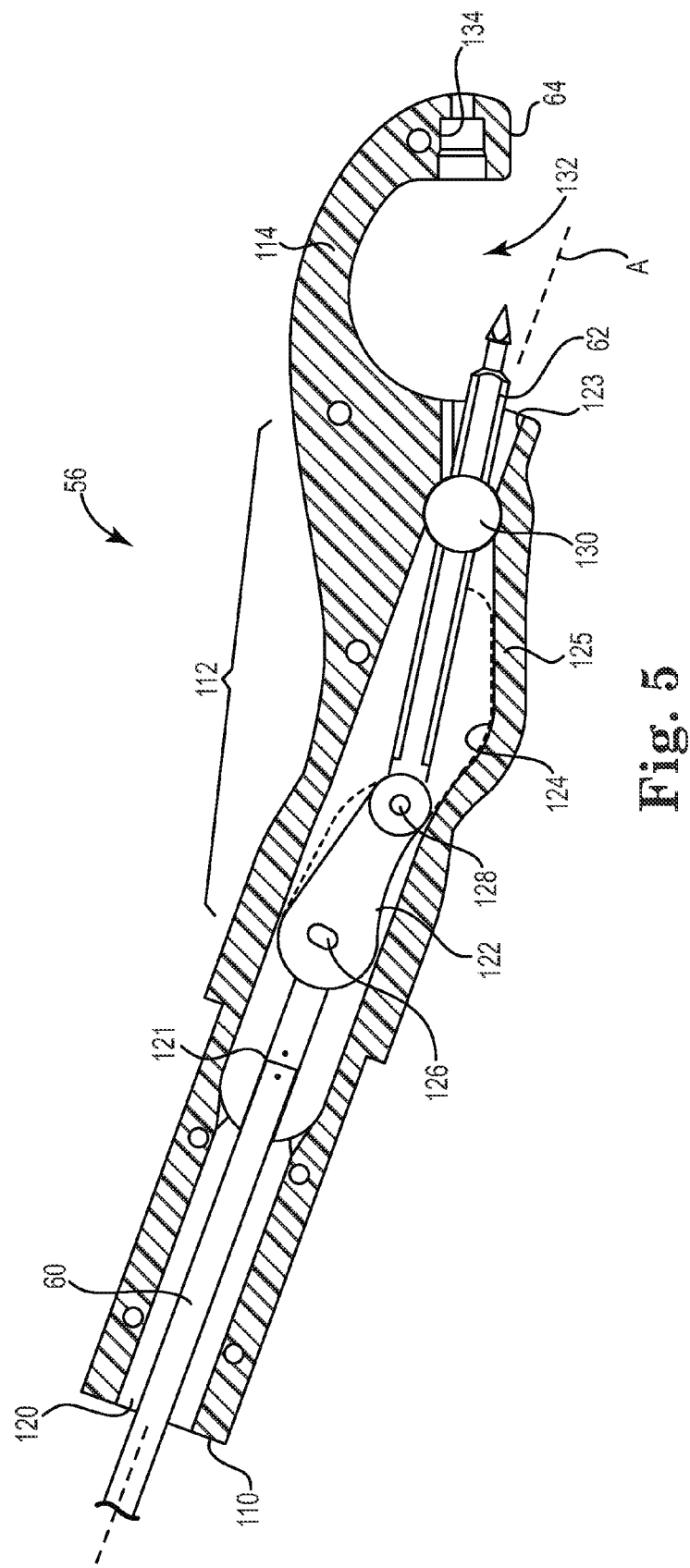
FIG. 5 is a cross-sectional view of a suture head of the suture thrower illustrated in FIG. 2.

FIG. 5 is a cross-sectional view of head 56. In one embodiment, head 56 is formed of two mating components, and the view of FIG. 5 is taken with one half of the structure removed so that the internal features of head 56 are visible. Head 56 is molded from plastic, for example from a polyetherimide plastic sold under the trademark Ultem, or from glass-filled polyetherimide plastics also sold under the trademark Ultem.

In one embodiment, the proximal end portion 112 extends from a proximal end 110 of the head 56 and includes a neck 114 that extends between the proximal end portion 112 and the distal end 64 to form a throat 132 that is suited for engaging over or around ligament or other tissue. Head 56 is attachable to shaft 54, and in one embodiment includes an opening 120 sized to receive shaft 54 such that rod 60 extends into proximal end portion 112 and couples with a link 122 that is attached to needle 62. In one embodiment, distal end 64 is not aligned with, but is rather offset radially from longitudinal axis A, to more comfortably position shaft 54 for manipulation by the surgeon as head 56 is engaged with tissue.

In one embodiment, a clevis pin 121 connects a proximal end of link 122 to rod 60 and a distal end of link 122 is coupled to needle 62. Movement of rod 60 moves link 122, which moves needle 62 into and out of a needle exit port 123 formed in proximal end portion 112. In one embodiment, a trace 124 that is formed on an interior surface 125 of proximal end portion 112 of head 56, and link 122 is configured to translate and rotate within trace 124 to translate needle 62 along axis A and pitch needle up/down relative to axis A. For example, in one embodiment link 122 includes a first pin 126 that couples with clevis 121 and a second pin 128 that couples with needle 62. Axial movement of rod 60 translates to axial movement of link 122 and needle 62, and link 122 rotates about pins 126, 128 to shunt a path of needle 62 off of axis A.

Link 122 is thus configured to translate within trace 124 to move needle 62 in/out relative to needle exit port 123, and rotate relative to pins 126, 128 to direct movement of needle 62 up/down relative to longitudinal axis A. In one embodiment proximal end portion 112 includes a guide pin 130 that defines a bore sized to receive needle 62. Needle 62 is configured to slide through the bore formed in guide pin 130, and guide pin 130 is rotatable to allow needle 62 to pitch relative to longitudinal axis A as needle 62 moves axially, for example as needle 62 moves into engagement with distal end 64.

Neck 114 extends between proximal end portion 112 and distal end 64 and defines the throat 132. Needle 62 is movable from proximal end portion 112, out of needle exit port 123, across throat 132, and into a cavity 134 formed in distal end 64. Needle 62 is preferably machined from metal such as stainless steel or a shape memory alloy such as NiTiNOL (Nickel Titanium Naval Ordinance Laboratory), as examples.

In one embodiment, distal end 64 and cavity 134 are both radially spaced away from longitudinal axis A, and guide pin 130 rotates to enable needle 62 to move out of the needle exit port 123, pitch upwards, and into cavity 134. In one embodiment, a top surface of neck 114 defines an open, exposed groove configured to receive and guide suture that extends from the capsule 28 (FIG. 6) captured in cavity 134 back to handle 52 (FIG. 1).

The cavity 134 is configured to retain the capsule 28 attached to suture 26 (see FIG. 1), and needle 62 is configured to penetrate tissue and enter cavity 134, engage the capsule 28, and pull the capsule 28 through the tissue and into needle exit port 123 to "throw" the suture across throat 132. The guide pin 130 is placed to displace the capsule 28 from the needle 62 when the knob 80 (FIG. 3) is rotated, which allows the surgeon or the technician to selectively disengage the capsule 28 from the head 56 of the suture thrower 50. Some embodiments of head 56 include mechanisms configured to linearly direct needle 62 out of needle exit port 123 across throat 132 and into cavity 134 for engagement with the capsule. Other embodiments of head 56 include mechanisms configured to shunt needle 62 (e.g., pitch needle 62 upward relative to axis A away from needle exit port 123 and into cavity 134 for engagement with the capsule).

Figure 6:
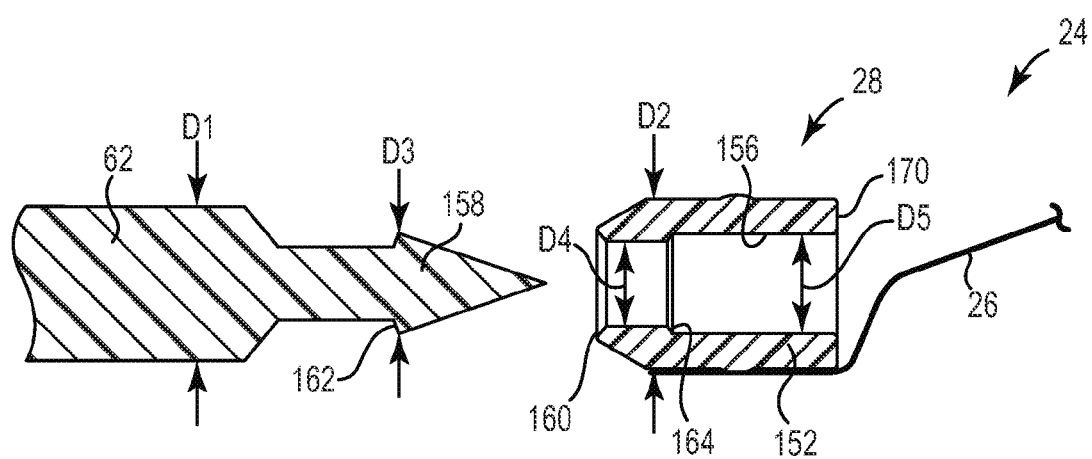
FIG. 6 is a cross-sectional view of one embodiment of a capsule of the suture attachment assembly illustrated in FIG. 1.

FIG. 6 is a side view of one embodiment of the needle 62 aligned for engagement with the capsule 28 of the suture attachment assembly 24. The needle 62 is employed to form the opening in the tissue and the capsule 28 is retrieved through the opening in the wake of the needle 62.

The capsule 28 is sized to be deposited and retained in cavity 134 (FIG. 5) of the head 56 of the suture thrower 50 to position the through-bore 156 to receive a leading end 158 of needle 62. In contrast to pointed, solid needles that are pushed through tissue, the capsule 28 is an annular tube segment having the through-bore 156 that configures the capsule 28 to be captured by the needle 62 and pulled through an opening that is pre-formed in the tissue by the needle 62. The structure of the capsule 28 allows the surgically sharp needle 62 to form a uniform opening in the tissue with the desirable benefit of a minimum of tissue trauma prior to engaging with the capsule 28 and retrieving the capsule 28 through the opening. Thus, the structure of the annular capsule 28 and the method of retrieving the annular capsule 28 through the opening in the tissue are counter-intuitive to the current approaches of driving bullet-shaped suture ends through tissue.

The through-bore 156 is formed as a longitudinal bore extending though the body of the capsule 28. In one embodiment, needle 62 is shaped to promote secure engagement with capsule 28 and leading end 158 is formed to have a conical point with a shoulder 162 that is sized to be pressed into engagement with a flange 164 of through-bore 156. For example, flange 164 that is shaped and sized to frictionally engage (e.g., snap-fit) in a "locked" manner with a shoulder 162 of needle 62 as needle 62 is driven into through-bore 156. Capsule 28 is configured to be detached from needle 62 by guide pin 130 (FIG. 5) after needle 62 pulls capsule 28 rearward in a proximal direction into head 56.

The conical point of needle 62 is configured to form a channel opening when advanced through tissue, and capsule 28 is sized to be pulled through the channel in the tissue made by needle 62. In one embodiment, leading end 160 of capsule 28 is chamfered and needle 62 is configured to draw the chamfered (or truncated) end 160 of capsule 28 first through the tissue. In one embodiment, leading end 160 of capsule 28 is a blunt end similar to that illustrated for the trailing end of the capsule 28, and needle 62 is configured to draw the blunt end 160 of capsule 28 blunt end-first through the tissue.

For example, in one embodiment needle 62 has a first diameter D1 and capsule 28 has a diameter D2, were diameter D1 is equal to or greater than diameter D2. In this manner, capsule 28 is sized to follow needle 62 and be retracted through the channel formed in the tissue by needle 62.

Leading end 158 of needle 62 is sized to frictionally engage with through-bore 156 formed in capsule 28. For example, in one embodiment leading end 158 has a diameter D3 that is slightly greater than an inside diameter D4 formed in an opening of through-bore 156. In this manner, when leading end 158 of needle 62 is inserted into through-bore 156, leading end 158 is forced into and seats within and captures capsule 28.

In one embodiment, the inside diameter D4 of the through-bore 156 adjacent to the leading end 160 of the capsule 28 is smaller than an inside diameter D5 of the through-bore 156 adjacent to the trailing end 170 of the capsule 28.

In one embodiment, the capsule 28 is molded from plastic integrally over the suture 26. Suitable plastic materials for fabricating capsule 28 include polypropylene, polysulfone, urethane, or polyetherimide as examples. Suture 26 includes monofilament suture, braided suture, coated suture materials or the like, as examples. In one embodiment, the suture 26 is a monofilament polypropylene suture.

Figure 7A:
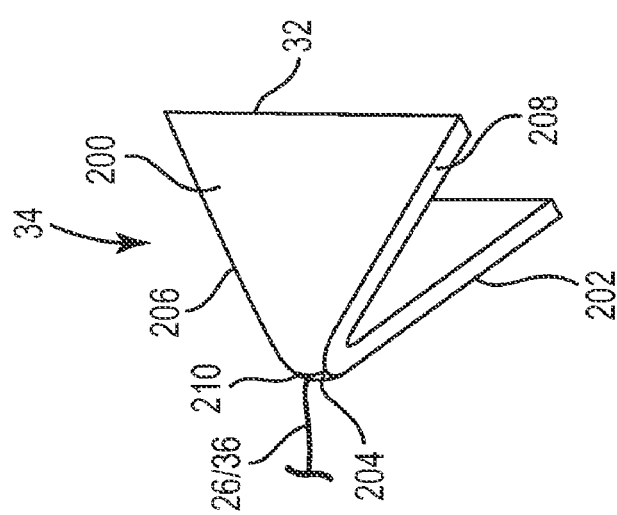
FIG. 7A is a perspective view.
Figure 7B:
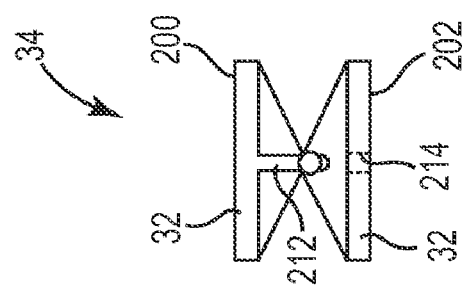
FIG. 7B is a front view.
Figure 7C:
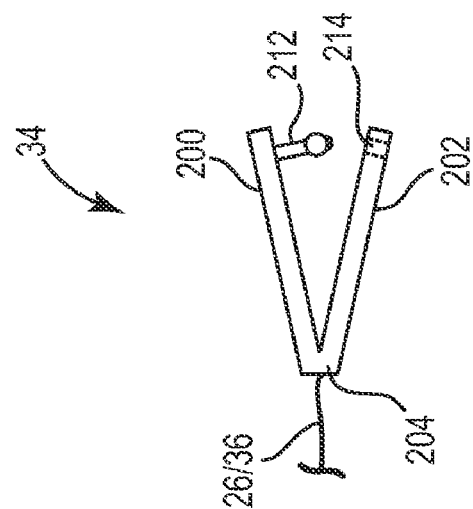
FIG. 7C is a side view of one embodiment of a clasp of the suture attachment assembly illustrated in FIG. 1.

FIG. 7A is a perspective view, FIG. 7B is a front view, and FIG. 7C is a side view of one embodiment of the clasp 34. In one embodiment, the clasp 34 is formed as a single monolithic unit including a first paddle 200 connected to a second paddle 202 by a spine 204. Each of the paddles 200, 202 of the single monolithic unit is formed to include sides 206, 208 that converge to a leading end 210 of the clasp 34 and diverge to a blunt trailing end, or anchor 32, of the clasp 34. The leading end 210 is sized to be wedged or pulled through the opening formed in the tissue by the needle 62 (FIG. 6), and the blunt anchor end 32 of the clasp 34 is sized to prevent the clasp 34 from being retracted back through the opening formed in the tissue.

In one embodiment, the first paddle 200 includes a projection 212 that is sized to frictionally engage with a recess 214 formed in the second paddle 202. For example, in one embodiment the first paddle 200 includes an exterior surface opposite an interior surface, and the projection 212 projects from the interior surface of the first paddle 200. In a similar manner, the second paddle 202 includes an exterior surface opposite an interior surface, and the recess 214 extends between the exterior surface and the interior surface. The projection 212 is formed to frictionally engage with the recess 214, for example by having a diameter that is slightly larger than a diameter of the recess 214, to allow the first paddle 200 to snap-fit into engagement with the second paddle 202.

The clasp 34 is fabricated from a material that is suitable for implantation into the human body. In one embodiment, the clasp 34 is fabricated from polypropylene. Other suitable materials for fabricating the clasp 34 include polyethylene, polymers in general, bio-absorbable polymers, biodegradable polymers, or bio-resorbable polymers.

FIGS. 8A-8E are schematic views of embodiments of the suture thrower 50 and the suture attachment assembly 24 employed to place an implantable fabric 22 into intracorporeal tissue.

Embodiments of the suturing device described herein provide a method of suturing tissue useful in many surgical procedures, including the treatment of pelvic dysfunction including pelvic organ prolapse. For example, embodiments provide a suturing device suited for the surgical treatment of pelvic organ prolapse that is operable to suture a scaffold or other support to a ligament or other tissue located within the pelvis. With some surgical procedures it is desirable to apply sutures to the sacrospinous ligament and/or the arcus tendineus ligament to attach a synthetic scaffold thereto that is configured to support the pelvic floor and reduce or eliminate the undesirable effects of pelvic organ prolapse.

During an exemplary procedure, a catheter is placed in the patient's urethra and other recommended, desirable, or preliminary surgical steps are taken in preparation for surgery. The patient is typically placed on an operating table in a lithotomy position with buttocks extending just beyond an edge of the table. With the patient under anesthesia, a vaginal incision (female) or a perineal incision (male) is made by the surgeon. Thereafter, the surgeon would typically palpate the patient to identify a desired landmark, such as the sacrospinous ligament or arcus tendineus ligament or other tissue landmark. The surgeon identifies the landmark, for example with a finger, and subsequently introduces sterile instrument 50 and engages the throat 132 (FIG. 5) of the head 56 with the identified landmark.

Figure 8A:
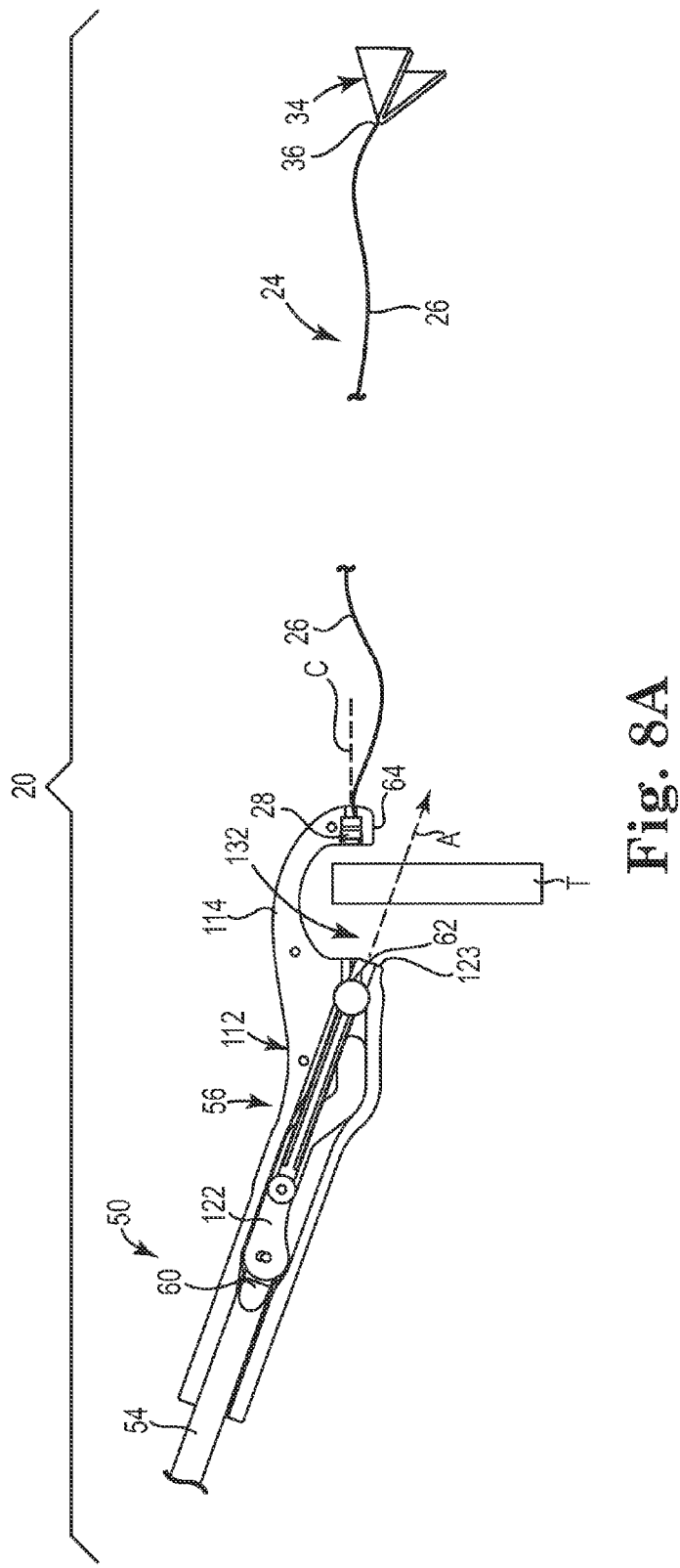
FIG. 8A is a schematic view of the suture head of the suture thrower engaged with intracorporeal tissue.

FIG. 8A is a schematic view of the throat 132 of the head 56 engaged with tissue T. The needle 62 is retracted within needle exit port 123 of proximal end portion 112 of head 56. Capsule 28 is seated in cavity 134 with suture 26 trailing distally away from head 56. The head 56 has been introduced into an incision and the throat 132 of the head 56 is placed to engage a portion of intracorporeal tissue T, which positions the needle 62 to capture the capsule 28 and pull the suture 26 through the intracorporeal tissue T. The intracorporeal tissue T includes soft tissue in general, such as the Cooper's ligament, the sacrospinous ligament, the arcus tendineus ligament, or other pelvic tissue.

In one embodiment, prior to throwing suture 26, it is recommended that the surgeon direct the trailing end 36 of suture 26 and clasp 34 over distal end 64 of head 56 and back toward a proximal end of shaft 54 for ease of managing suture attachment assembly 24 during the procedure. To facilitate this, in one embodiment the distal end 64 of the head 56 includes a slot configured to enable the suture 26 to pass through distal end 64 to facilitate loading/unloading capsule 28 into cavity 134.

In one embodiment, rod 60 and needle 62 are aligned on axis A when needle 62 is retracted into proximal end portion 112 as illustrated, and capsule 28 is aligned on an axis C that is not aligned with axis A.

Figure 8B:
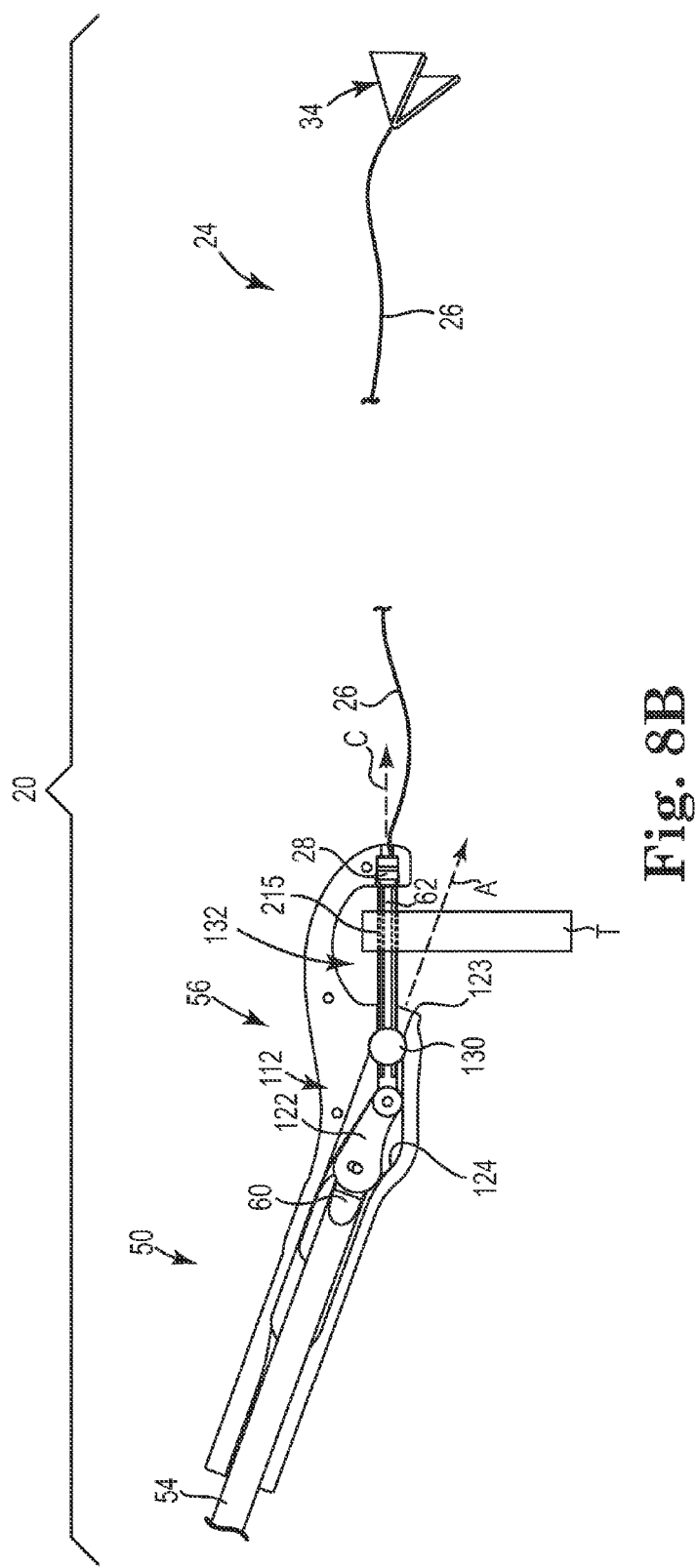
FIG. 8B is a schematic view of a needle of the suture had forming an opening in the intracorporeal tissue.

FIG. 8B is a schematic view of the system 20 with the needle 62 pushed through the tissue T to form an opening 215 in the tissue T. The needle 62 is shunted away from longitudinal axis A by link 122 and pin 130, moved in a second direction along axis C by rod 60, and translated through the intracorporeal tissue T to the distal end 64 of the head 56 for engagement with the through-bore 156 (FIG. 6) of the capsule 28. Guide pin 130 has rotated counterclockwise to allow the movement of link 122 within trace 124 to shunt the direction of needle 62 out of alignment with axis A and into alignment with axis C. Additional forward movement of rod 60 will further direct needle 62 across throat 132, through the intracorporeal tissue T, and into engagement with capsule 28. As described below, needle 62 is reversible along the paths coincident with axis C and axis A to retract needle 62 and capsule 28 into needle exit port 123.

FIG. 8C is a schematic view of needle 62 retracted into head 56 with capsule 28 parked in needle exit port 123 and the suture 26 thrown through the intracorporeal tissue T. In one embodiment, needle exit port 123 is sized to receive capsule 28 such that port 123 forms a capsule garage 123 into which capsule 28 is parked after extraction from cavity 134. Rod 60 has drawn link 122 into full rearward engagement with trace 124 such that needle 62 is aligned with axis A and retracted into head 56. Capsule 28 is parked inside needle exit port 123 and suture 26 extends across throat 132 and through the intracorporeal tissue T, which configures the system 20 to allow the surgeon to pull the head 56 and the capsule 28 out of the patient for subsequent manipulation of the capsule 28.

In one embodiment, and as described above with reference to FIG. 2, knob 80 is configured to be turned to incrementally retract rod 60 an additional distance into handle 52, which separates needle 62 from capsule 28. For example, the additional retraction of needle 62 by the rearward motion of rod 60 causes capsule 28 to be pressed against guide pin 130, which shears capsule 28 off of needle 62. Needle 62 is thus disengaged from capsule 28 to allow the surgeon to manipulate the capsule 28 free of the head 56 and outside of the patient's body.

Figure 8D:
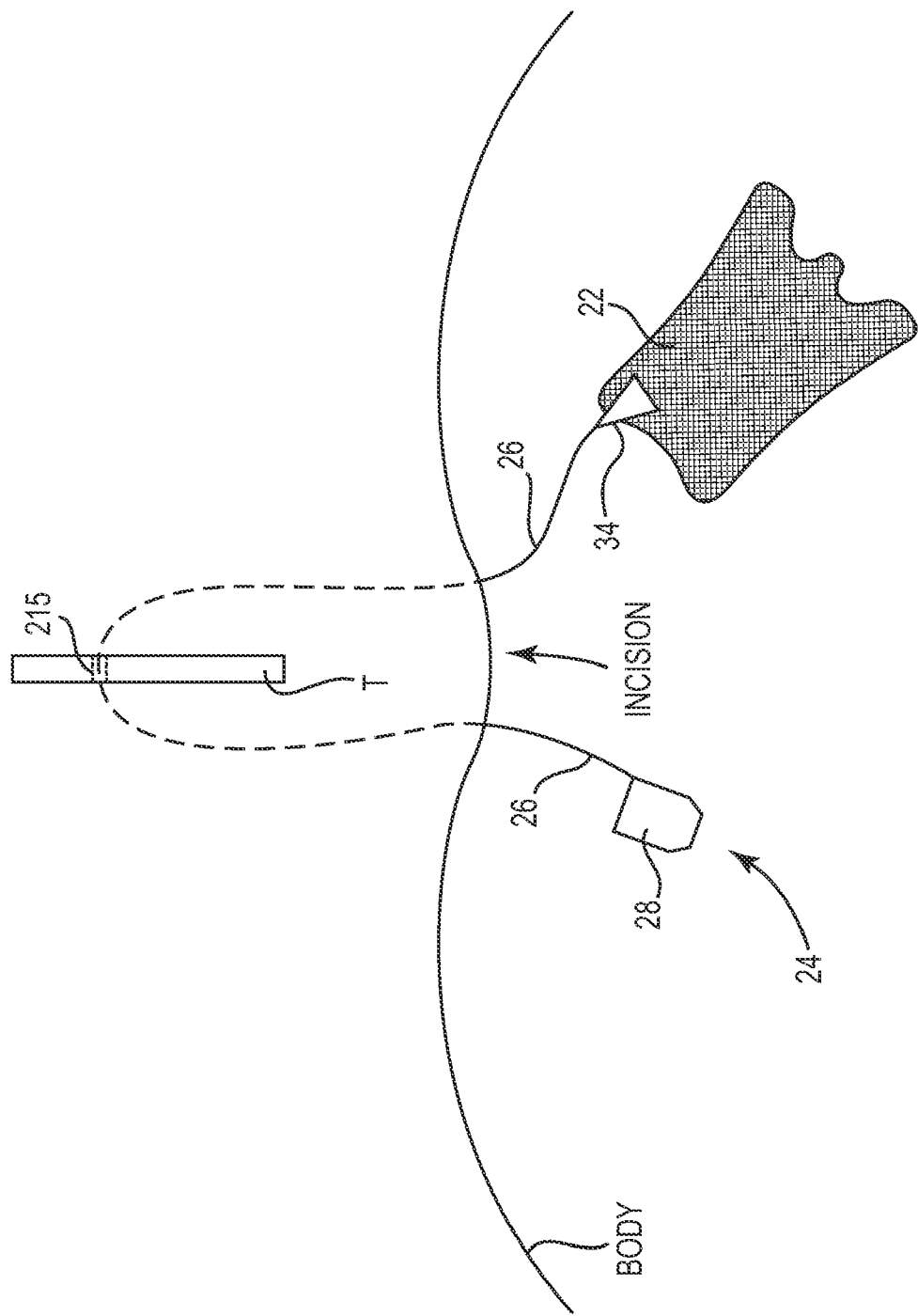
FIG. 8D is a schematic view of the capsule in the clasp located outside of the body with the clasp secured to the implantable support.

FIG. 8D is a schematic view of the suture attachment assembly 24 engaged with the intracorporeal tissue T. The capsule 28 and clasp 34 reside outside of the patient's body in the suture 26 enters the patient's body through the incision and disengaged with the intracorporeal tissue T. With reference to FIG. 7C, the surgeon may selectively attach the clasp 34 to a desired location of the implantable support 22 by snapping the first paddle 200 into engagement with the second paddle 202 to capture implantable support 22 between the paddles 200, 202. In this manner, pulling on the end of the suture 26 attached to the capsule 28 will pull the implantable support 22 into a desired location within the patient's body.

Figure 8E:
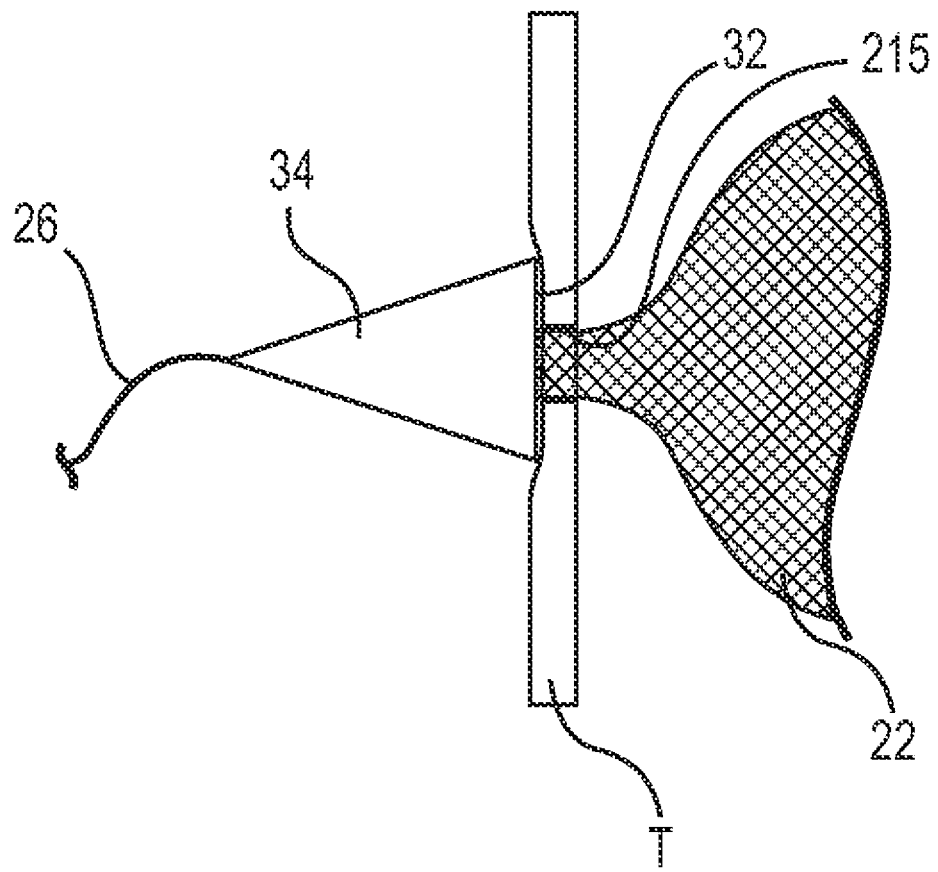
FIG. 8E is a schematic view of the anchor engaged with the back side of the intracorporeal tissue and the implantable support secured relative to the intracorporeal tissue T.

FIG. 8E is a schematic view of the clasp 34 pulled through the opening 215 formed in the intracorporeal tissue T by the needle 62 (FIG. 8B) until the anchor 32 is engaged with the back side of the tissue T to secure the implantable support 22 relative to the intracorporeal tissue T.

Embodiments have been described providing a method of intracorporeally suturing tissue of a patient, where the method includes engaging the tissue with a suturing head 56 retaining a needle 62, forming an opening 215 in the tissue T with the needle 62, passing a leading end of a suture 26 through the opening 215, securing a clasp 34 attached to a trailing end of the suture 26 to an implantable support 22, and pulling the suture 26 and an anchor 32 that is attached to the suture 26 through the opening 215 formed in the tissue T, thus placing the implantable support 22 inside the patient.

In one embodiment, the clasp 34 is a tissue or a biologic body including attached synthetic arms, where the clasp 34 assists in placing the attached synthetic arms into the patient and the synthetic arms include a portion of, or all of, the implantable fabric 22.

FIGS. 8F-8I are schematic views of embodiments of the suture attachment assembly 24 (as placed by the suture thrower 50 described above) employed to place another implantable fabric 22' into intracorporeal tissue.

FIG. 8F is a schematic view of the clasp 34 of the suture attachment assembly 24 positioned for engagement with a sacrificial tab 216 that extends from the implantable fabric 22'. The surgeon attaches the clasp 34 to the sacrificial tab 216 of the implantable support 22' by snapping the first paddle 200 into engagement with the second paddle 202 (FIG. 7C) to capture the sacrificial tab 216 between the paddles 200, 202. The implantable support 22' is pulled to a desired location and implanted within the patient's body when the surgeon pulls on the end of the suture 26 that is attached to the capsule 28. The suture attachment assembly 24 and the sacrificial tab 216 of the implantable fabric 22' are both removed from the patient's body.

Figure 8G:
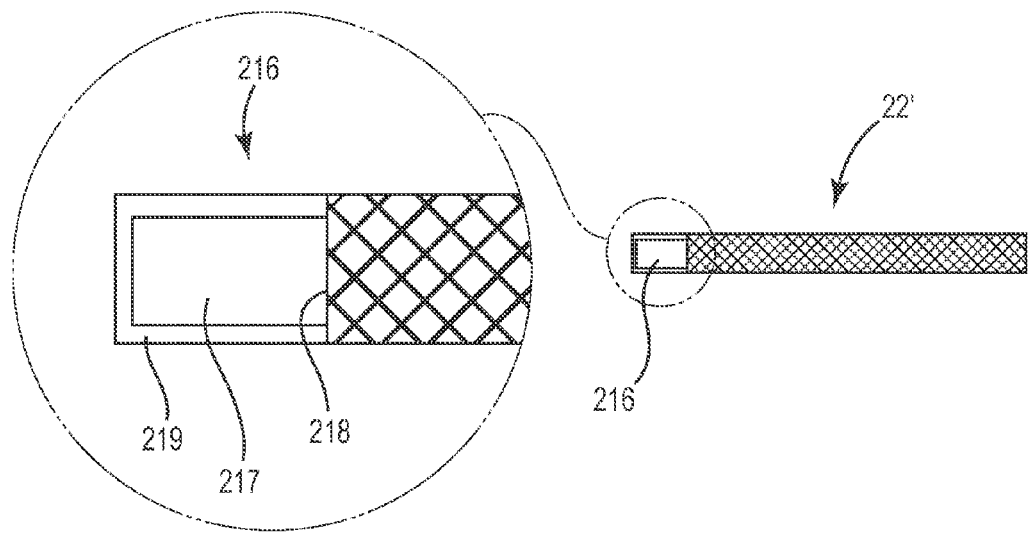

FIG. 8G is a side view of the sacrificial tab 216 portion of the implantable fabric 22'. In one embodiment, the sacrificial tab 216 includes tab material 217 that is attached to the implantable fabric 22' along a break line 218. In one embodiment, the tab material 217 is sheathed in material 219 that is configured to assist in pulling the sacrificial tab 216 through tissue. For example, in one embodiment the sheath material 219 is a coating of a polyvinyl alcohol film that is applied over the tab material 217 to provide lubricity between the sacrificial tab 216 and the tissue as the sacrificial tab 216 is pulled or placed in the tissue. In one embodiment, the entire sacrificial tab 216, including the sheath material 219, is removed from the implantable fabric 22' after implantation. However, any polyvinyl alcohol film sheath material 219 that remains in the patient's body after implantation is configured to dissolve and be absorbed into the patient's body.

Figure 8H:
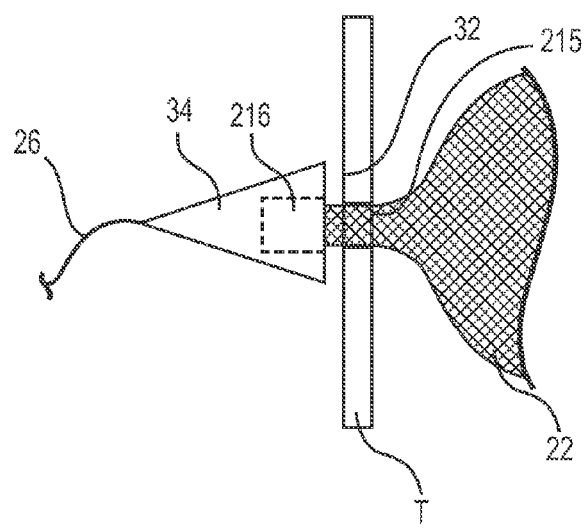

FIG. 8H is a schematic view of the clasp 34 attached to the sacrificial tab 216 and pulled through the opening 215 that was formed in the intracorporeal tissue T by the needle 62 (FIG. 8B). The implantable fabric 22' is secured or seated in the tissue T.

Figure 8I:
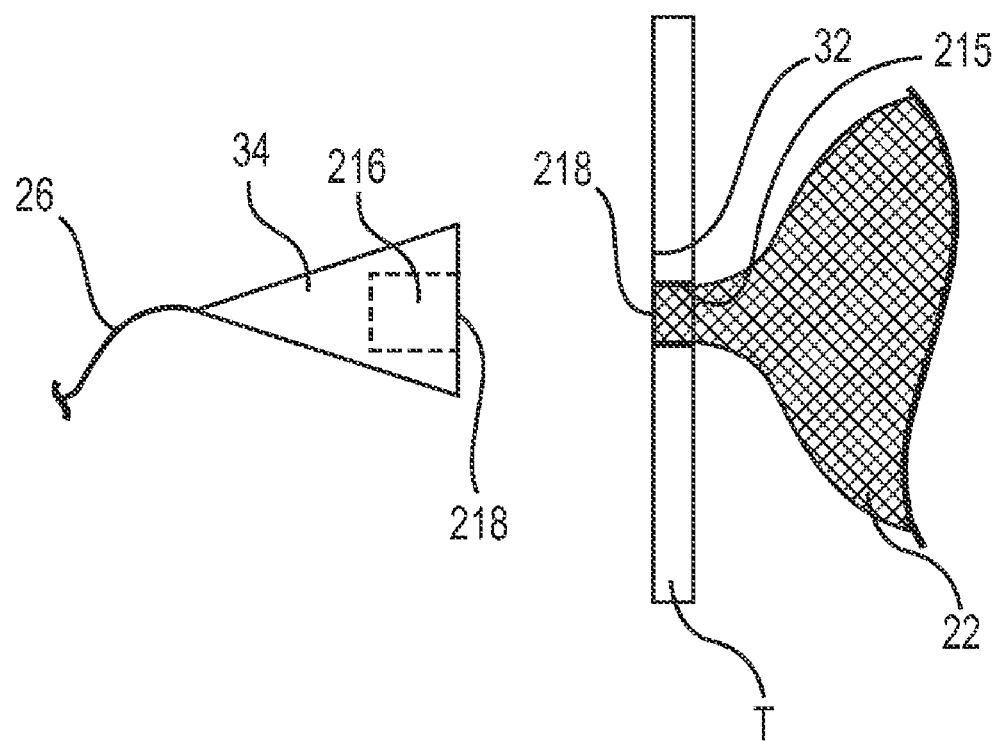

FIG. 8I is a schematic view of the clasp 34 and the sacrificial tab 216 pulled through the tissue T and separated at the break line 218. The implantable fabric 22' is thus implanted in the tissue T and the entire suture attachment assembly 24, including the clasp 34 and the sacrificial tab 216, are removed from the patient and disposed of.

Figure 9:
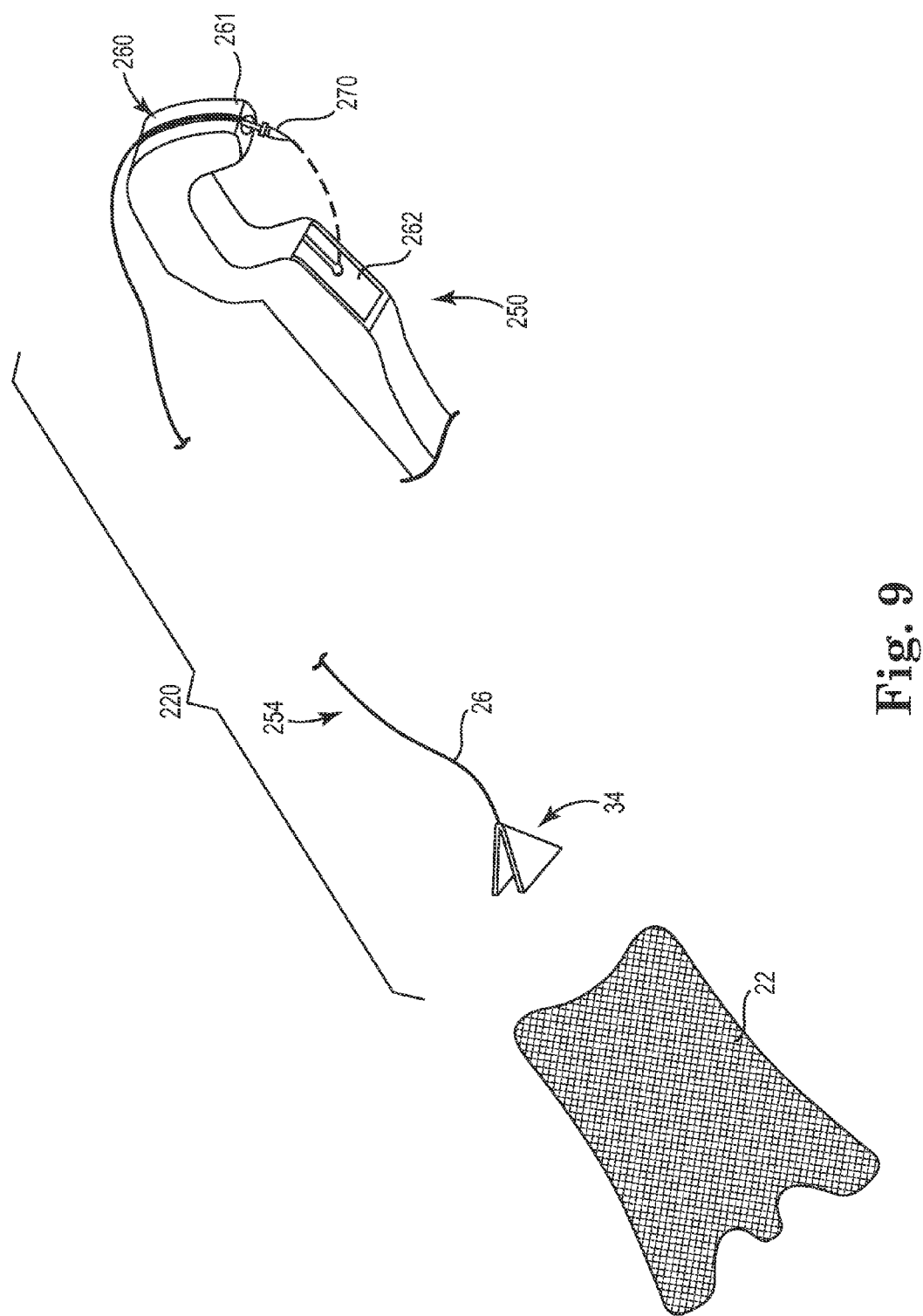
FIG. 9 is a schematic view of an implantable support attachment system including the suture attachment assembly illustrated in FIG. 1 and one embodiment of a suture thrower.

FIG. 9 is a schematic view of one embodiment of an attachment system 220 configured to secure the implantable support 22 within a patient. The attachment system 220 includes a suture capturing device 250 and a suture attachment assembly 254.

The suture capturing device 250 includes a needle driver 260 having a distal tip 261 spaced apart from a catch mechanism 262. The suture attachment assembly 254 includes a needle 270 or a bullet 270 attached to a leading end of the suture 26 with the clasp 34 attached to the trailing end of the suture 26. The implantable support 22 is as described above.

In one embodiment, the needle driver 260 is designed to place a sling transvaginally by throwing the suture 26 through the Cooper's ligament, for example. The needle 270 is loaded into the distal tip 261 of the needle driver 260, and upon activation of the needle driver 260 (for example by an activation mechanism in a handle of the driver 260) the bullet 270 is delivered in an arc across the throat and retained within the catch mechanism 262. In this manner, the needle 270 and the suture 26 are both thrown through the tissue and the needle 270 is retained within the catch mechanism for retrieval to a location outside of the patient's body. Thereafter, the surgeon attaches the clasp 34 to implant 22, imposed a needle 270 the catch mechanism 262, and pulls the suture 26 through the tissue to implant to support 22.

FIG. 10A is a perspective view, FIG. 10B is a front view, and FIG. 10C is a side view of one embodiment of a clasp 294 suited for use with the system 20 and the suture attachment assembly 24 illustrated in FIG. 1.

In one embodiment, the clasp 294 is formed as a single monolithic unit including a first paddle 300 connected to a second paddle 302 by a spine 304. Each of the paddles 300, 302 of the single monolithic unit is formed to include sides 306, 308 that converge to a leading end 310 of the clasp 294 and diverge to a blunt trailing end 311, or anchor 311, of the clasp 294. The leading end 310 is sized to be wedged or pulled through tissue, and the anchor end 311 of the clasp 294 is sized to prevent the clasp 294 from being retracted back through the tissue.

In one embodiment, the first paddle 300 includes a projection 312 that is sized to frictionally engage with a recess 314 formed in the second paddle 302. For example, in one embodiment the first paddle 300 includes an exterior surface opposite an interior surface, and the projection 312 projects from the interior surface of the first paddle 300. In a similar manner, the second paddle 302 includes an exterior surface opposite an interior surface, and the recess 314 extends between the exterior surface and the interior surface. The projection 312 is formed to frictionally engage with the recess 314 to allow the first paddle 300 to snap-fit into engagement with the second paddle 302.

In one embodiment, the clasp 294 has a curved anchor end 311. The leading end 310 of the clasp 294 is attached to the trailing end 36 of the suture 26, and each of the paddles 300, 302 is provided with a curved anchor end 311 having a pair of spaced apart prongs 316, 318. Each of the prongs 316, 316 is configured to engage with the intracorporeal tissue after the clasp 294 has been pulled through the tissue to ensure that the clasp 294 remains fixed at the implant site selected by the surgeon.

FIG. 11A is a top view, FIG. 11B is a side view, and FIG. 11C is a perspective view of one embodiment of a clasp 324 suited for use with the system 20 and the suture attachment assembly 34 illustrated in FIG. 1.

In one embodiment, the clasp 324 is formed as a single monolithic unit including a first paddle 330 connected to a second paddle 332 by a spine 334. Each of the paddles 330, 332 of the single monolithic unit is formed to include sides 336, 338 that converge to a leading end 340 of the clasp 324 and diverge to an anchor 341 of the clasp 324. The leading end 340 is sized to be wedged or pulled through tissue, and the anchor 341 is sized to prevent the clasp 324 from being retracted back through the tissue.

In one embodiment, the first paddle 330 includes projections 342, 343 that are each sized to frictionally engage with a complementary recess 344 formed in the second paddle 332. The projections 342, 343 are formed to frictionally engage with the recesses 344 to allow the first paddle 330 to snap-fit into engagement with the second paddle 332 to capture the support 22 (FIG. 1) there between.

In one embodiment, the leading end 340 of the clasp 324 is attached to the trailing end 36 of the suture 26, and the anchor 341 is located between the leading end 340 and a trailing end 346 of the clasp 324. In this manner, when the suture 26 is pulled through the opening 215 formed in the intracorporeal tissue T (FIG. 8B) by the needle 62, the leading end 340 of the clasp 324 will pass through the opening 215 and the anchor 341 will become engaged with the tissue T. The trailing end 346 of the clasp 324 and a portion of the paddles 330, 332 will not be pulled through the tissue T. In other words, the anchor 341 is configured to engage with the tissue such that the leading end 340 projects out of one side of the ligament, for example, and the trailing end 346 of the paddles 330, 332 project out of the other side of the ligament. The support 22 is consequently not pulled through the tissue. The clasp 324 thus provides a mid-located anchor 341.

FIG. 12A is a top view and FIG. 12B is a side view of another embodiment of a suture attachment assembly 350. The suture attachment assembly 350 includes the suture line 26, the capsule 28 attached to the leading end 30 of the suture line 26, a clasp 354 attached to the trailing end 36 of the suture line 26, and an anchor 352 that is attached to the suture line 26 and separate from the clasp 354. The suture line 26 and the capsule 28 are described above, and are employed to pull the anchor 352 and the clasp 354 to an intracorporeal location within the patient's body.

In one embodiment, the anchor 352 is conical or bullet-shaped or converges to a pointed leading end 356 that is configured to allow the anchor 352 to be pulled through an opening formed in the tissue. A trailing end 358 of the anchor 352 is configured to be wider than the leading end 356 such that the anchor 352 prevents the leading portion of the suture attachment assembly 350 from being pulled back through the opening in the intracorporeal tissue. In one embodiment, the anchor 352 is a conical anchor fabricated from polypropylene.

In one embodiment, the clasp 354 is configured to open and close and includes a first paddle 360 attached to a second paddle 362 by a spine 364. In one embodiment, spine 364 is provided as a "living hinge" that allows the first paddle 360 and the second paddle 362 to flex relative to the spine 364. In one embodiment, the first paddle 360 includes a projection 370 projecting from an interior surface that is configured to engage with a recess 372 formed in the second paddle 362. The clasp 354 opens wide enough to receive the implantable support 22 (FIG. 1) and the paddles 360, 362 are configured to close down upon and engage implantable support 22 to secure the support inside of the clasp 354.

During implantation, and as described above, the capsule 28 is pulled or thrown through an opening formed in the intracorporeal tissue by the needle 62 (FIG. 6) and retrieved a location outside of the patient's body. The capsule 28 allows the suture line 26 to be pulled through the opening in the intracorporeal tissue to place the support material held within the clasp 354 at the desired intracorporeal location.

In one embodiment, the anchor 352 slides along the suture 26. For example, during placement of the anchor 352, the anchor 352 is pulled through the opening formed in the intracorporeal tissue and then manually pushed along the suture 26 toward the clasp 354 to secure the clasp 354 at the desired intracorporeal location.

FIG. 13 is a side view of another embodiment of a suture attachment assembly 380. The suture attachment assembly 380 includes the suture line 26, the capsule 28 attached to the leading and 30 of the suture 26, and a plate 382 attached to the trailing end 36 of the suture 26. In one embodiment, the plate 382 includes projections 384 formed along an exterior surface of the plate 382. The projections 384 are configured to engage with woven or nonwoven support fabrics that are suitable for implantation into the human body. In this embodiment, the plate 382 provides a clasp with one paddle, where the one paddle includes projections that are configured to engage with threads or other portions of an implantable body support.

Embodiments of a suture attachment system and assembly have been described that allow a surgeon to secure an implantable support within a patient while offering improved implant management that is more intuitive and accurate in placement and less complex and cumbersome.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of intracorporeally suturing a patient, the method comprising:
    engaging tissue with a suturing head retaining a needle;
    forming an opening in the tissue with the needle;
    pushing the needle out of a needle exit port formed in a proximal end portion of the suturing head;
    directing the needle along a longitudinal axis of the suturing head;
    pitching the needle off of the longitudinal axis of the suturing head;
    engaging the needle with a through-bore formed longitudinally through a capsule that is attached to a leading end of a suture and pulling the capsule and the leading end of the suture through the opening;
    securing a clasp attached to a trailing end of the suture to an implantable support; and
    pulling on the suture and implanting the support inside the patient.

2. The method of claim 1, wherein pulling on the suture comprises pulling an anchor that is attached to the suture at least part way through the opening formed in the tissue.

3. The method of claim 2, comprising pulling the anchor that is attached to the suture from a first side of the tissue through to a second opposite side of the tissue, and implanting the support on the second opposite side of the tissue.

4. The method of claim 2, wherein the anchor is integrally formed on a leading end of the clasp.

5. The method of claim 4, wherein pulling an anchor that is attached to the suture at least part way through the opening formed in the tissue comprises pulling the leading end of the clasp through the opening formed in the tissue.

6. The method of claim 1, comprising driving the needle from the proximal end portion of the suturing head through the tissue and into engagement with the capsule retained in a distal end of the suturing head.

7. The method of claim 1, comprising pressing the implantable support between two opposing paddles of the clasp.

8. The method of claim 7, comprising pressing a projection extending from a first paddle of the clasp into engagement with a recess formed in a second paddle of the clasp.

9. The method of claim 1, comprising intertwining a projection extending from a plate of the clasp into engagement with threads of the implantable support.

10. The method of claim 1, comprising securing the clasp to a sacrificial tab that is attached to the implantable support along a break line.

11. The method of claim 10, further comprising:
separating the clasp and the sacrificial tab from the implantable support and removing the clasp and the sacrificial tab from the patient.

12. The method of claim 1, further comprising pulling the leading end of the suture out of the patient.

13. The method of claim 12, further comprising guiding the clasp secured to the implantable support from a location outside of the patient to a location inside the patient.

14. The method of claim 1, wherein the through-bore comprises an axial through-bore, with the method further comprising:
pushing the needle into the axial through-bore; and
snap-fitting the needle into the axial through-bore.

* * * * *